United States Patent
Li et al.

(10) Patent No.: US 9,085,551 B2
(45) Date of Patent: Jul. 21, 2015

(54) SOLID FORMS OF 3-(4-NITRO-1-OXISOINDOLIN-2-YL)PIPERIDINE-2,6-DIONE

(71) Applicant: Celgene Corporation, Summit, NJ (US)

(72) Inventors: Ying Li, Springfield, NJ (US); Jean Xu, Warren, NJ (US); Kevin J. Klopfer, Flemington, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/380,033

(22) PCT Filed: Feb. 20, 2013

(86) PCT No.: PCT/US2013/026842
§ 371 (c)(1),
(2) Date: Aug. 20, 2014

(87) PCT Pub. No.: WO2013/126394
PCT Pub. Date: Aug. 29, 2013

(65) Prior Publication Data
US 2015/0094473 A1     Apr. 2, 2015

Related U.S. Application Data

(60) Provisional application No. 61/601,459, filed on Feb. 21, 2012.

(51) Int. Cl.
*C07D 401/04*     (2006.01)

(52) U.S. Cl.
CPC .......... *C07D 401/04* (2013.01); *C07B 2200/13* (2013.01)

(58) Field of Classification Search
None
See application file for complete search history.

(56) References Cited

U.S. PATENT DOCUMENTS

| 5,635,517 | A | 6/1997 | Muller et al. |
| 6,281,230 | B1 | 8/2001 | Muller et al. |
| 2011/0263649 | A1* | 10/2011 | Bhosale et al. ............... 514/323 |

FOREIGN PATENT DOCUMENTS

| WO | 2011/050962 A1 | 5/2011 |
| WO | 2011/111053 A1 | 9/2011 |

* cited by examiner

*Primary Examiner* — Timothy R Rozof
(74) *Attorney, Agent, or Firm* — Jones Day

(57) ABSTRACT

Solid forms comprising crystalline 3-(4-nitro-1-oxoisoindolin-2-yl)piperidine-2,6-dione are disclosed. Compositions comprising the solid forms, methods of making the solid forms and methods of their use are also disclosed.

5 Claims, 24 Drawing Sheets

Figure 1:
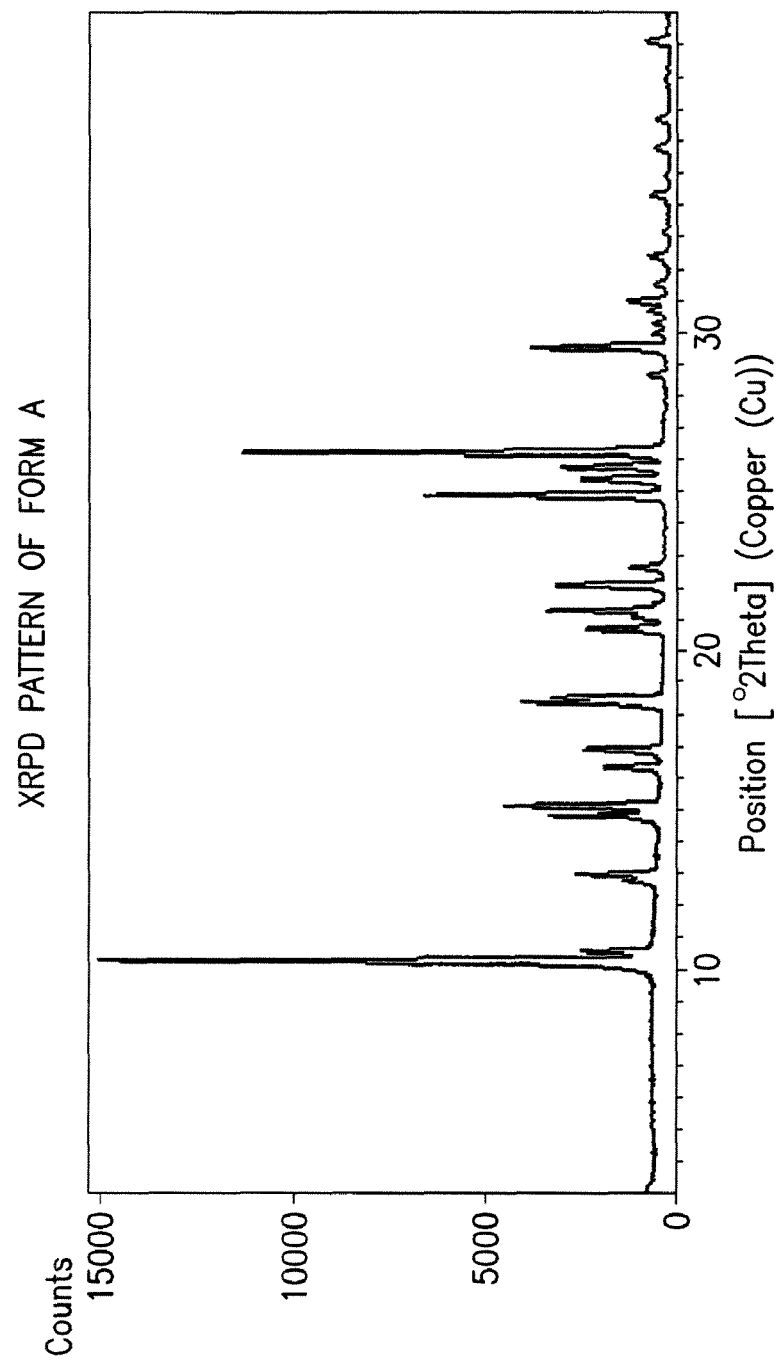

MORPHOLOGY OF FORM A
Form A 1000X
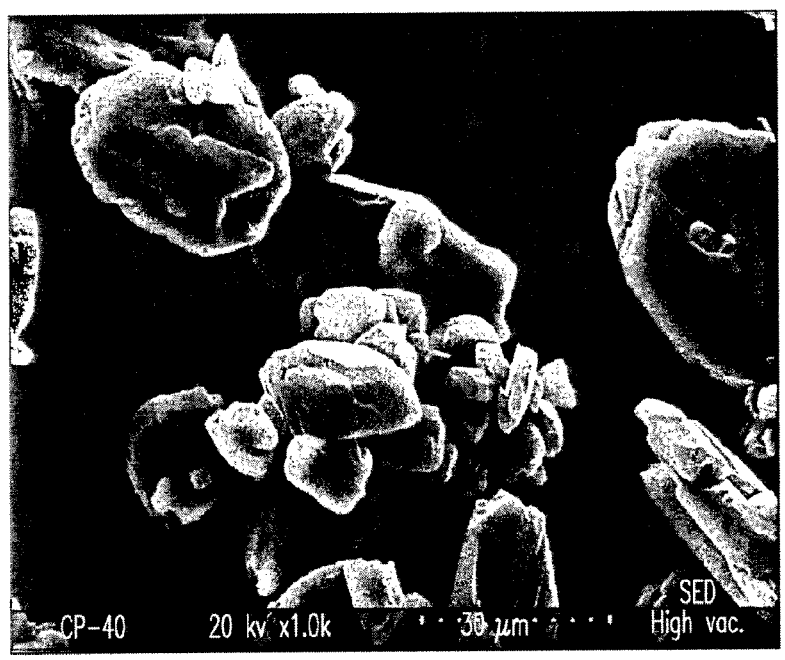
Form A 200X
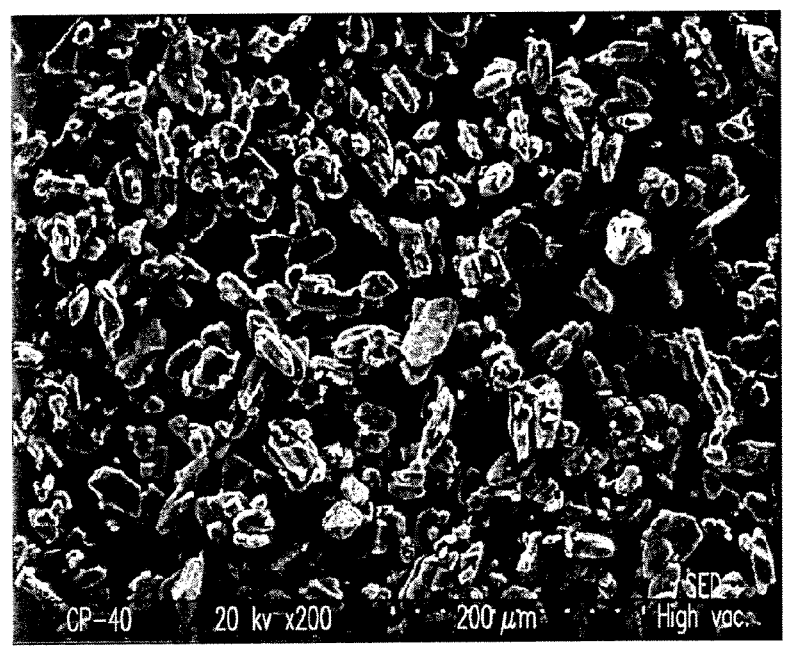
FIG. 2

MORPHOLOGY OF FORM B
Form B 1000X
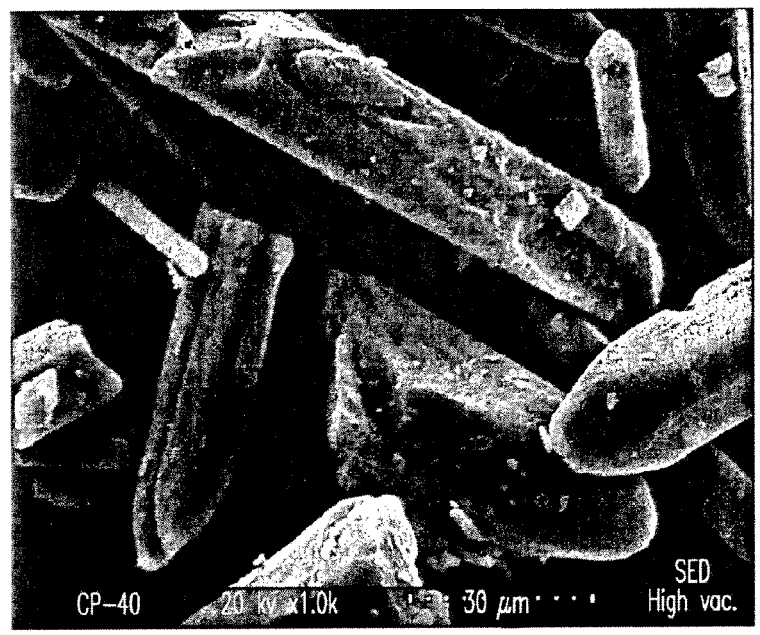
Form B 200X
FIG. 8

MORPHOLOGY OF FORM C
Form C 1000X
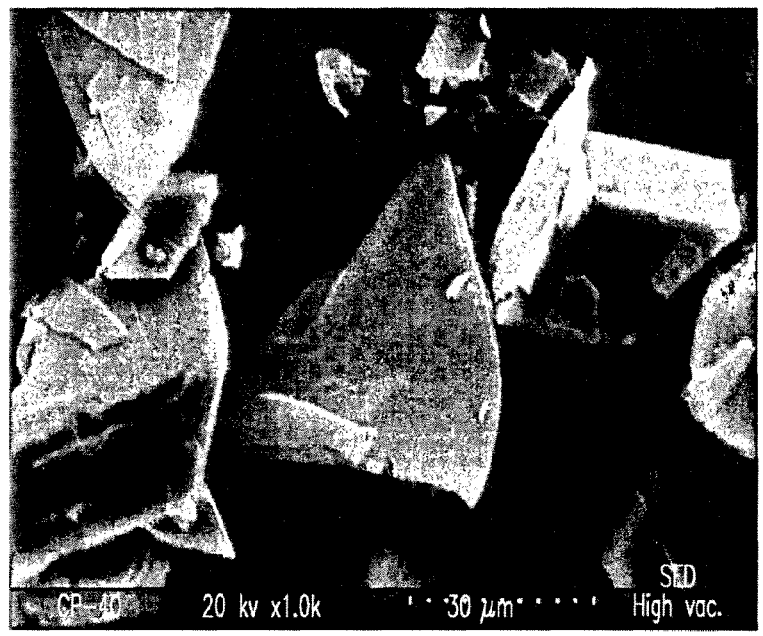
Form C 200X
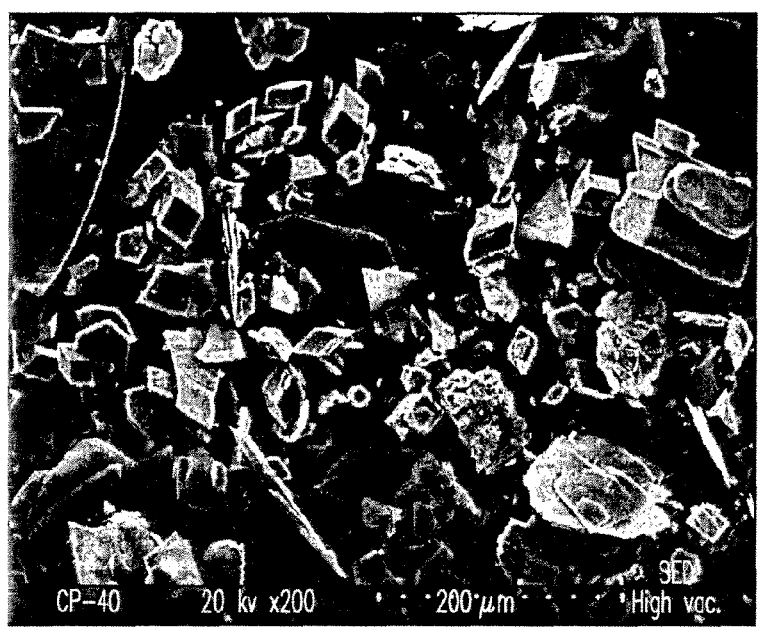
FIG. 15

US 9,085,551 B2

SOLID FORMS OF 3-(4-NITRO-1-OXISOINDOLIN-2-YL)PIPERIDINE-2,6-DIONE

This application is a national phase entry pursuant to 35 U.S.C. 371 of International Application No. PCT/US2013/026842, which has the international filing date of Feb. 20, 2013, which claims priority to U.S. Provisional Application No. 61/601,459, filed Feb. 21, 2012, the entireties of which are incorporated herein by reference.

1. FIELD

Provided herein are solid forms of 3-(4-nitro-1-oxoisoindolin-2-yl)piperidine-2,6-dione, compositions comprising the solid forms, methods of making the solid forms and methods of their use for the preparation of 3-(4-amino-1-oxoisoindolin-2-yl)piperidine-2,6-dione and for the treatment of diseases and conditions including, but not limited to, inflammatory diseases, autoimmune diseases, and cancer.

2. BACKGROUND

Compounds may exist in different solid forms. The selection of a solid form of a pharmaceutical compound may affect a variety of physical and chemical properties, which may provide benefits or drawbacks in processing, formulation, stability and bioavailability, among other important pharmaceutical characteristics. Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, potential solid forms of a pharmaceutical compound may include single-component and multiple-component solids. Single-component solids consist essentially of the pharmaceutical compound in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette).

Additional diversity among the potential solid forms of a pharmaceutical compound may arise from the possibility of multiple-component solids. Crystalline solids comprising two or more ionic species are termed salts (see, e.g., *Handbook of Pharmaceutical Salts: Properties, Selection and Use*, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., *Solid State Chemistry of Drugs*, (1999) SSCI, West Lafayette). Moreover, multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

U.S. Pat. Nos. 5,635,517 and 6,281,230, both to Muller et al., disclose 3-(4-nitro-1-oxoisoindolin-2-yl)piperidine-2,6-dione, which is useful in preparing 3-(4-amino-1-oxoisoindolin-2-yl)piperidine-2,6-dione, which is useful in treating and preventing a wide range of diseases and conditions including, but not limited to, inflammatory diseases, autoimmune diseases, and cancer. New polymorphic forms of 3-(4-nitro-1-oxoisoindolin-2-yl)piperidine-2,6-dione can further the preparation of 3-(4-amino-1-oxoisoindolin-2-yl)piperidine-2,6-dione and can further the development of formulations for the treatment of these chronic illnesses, and may yield numerous formulation, manufacturing and therapeutic benefits.

3. SUMMARY

In some embodiments, provided herein are solid forms of 3-(4-nitro-1-oxoisoindolin-2-yl)piperidine-2,6-dione. In some embodiments, provided herein are polymorphs of the compound identified herein as forms A, B, and C. In some embodiments, provided herein are mixtures of these forms. In further embodiments, provided herein are methods of making, isolating and characterizing the polymorphs.

In some embodiments, provided herein are pharmaceutical compositions and single unit dosage forms comprising a polymorph of 3-(4-nitro-1-oxoisoindolin-2-yl)piperidine-2,6-dione. In some embodiments, provided herein are methods for the treatment or prevention of a variety of diseases and disorders, which comprise administering to a patient in need of such treatment or prevention a therapeutically effective amount of a polymorph of 3-(4-nitro-1-oxoisoindolin-2-yl)piperidine-2,6-dione.

4. BRIEF DESCRIPTION OF THE FIGURES

Figure 3:
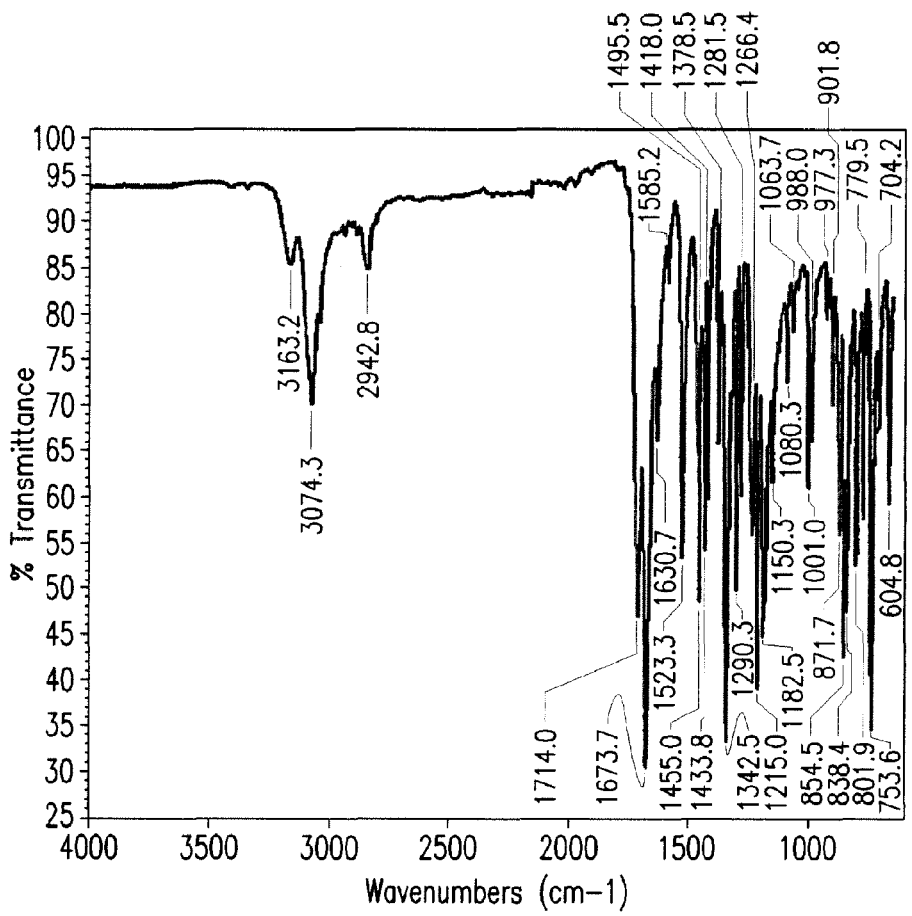
Figure 4:
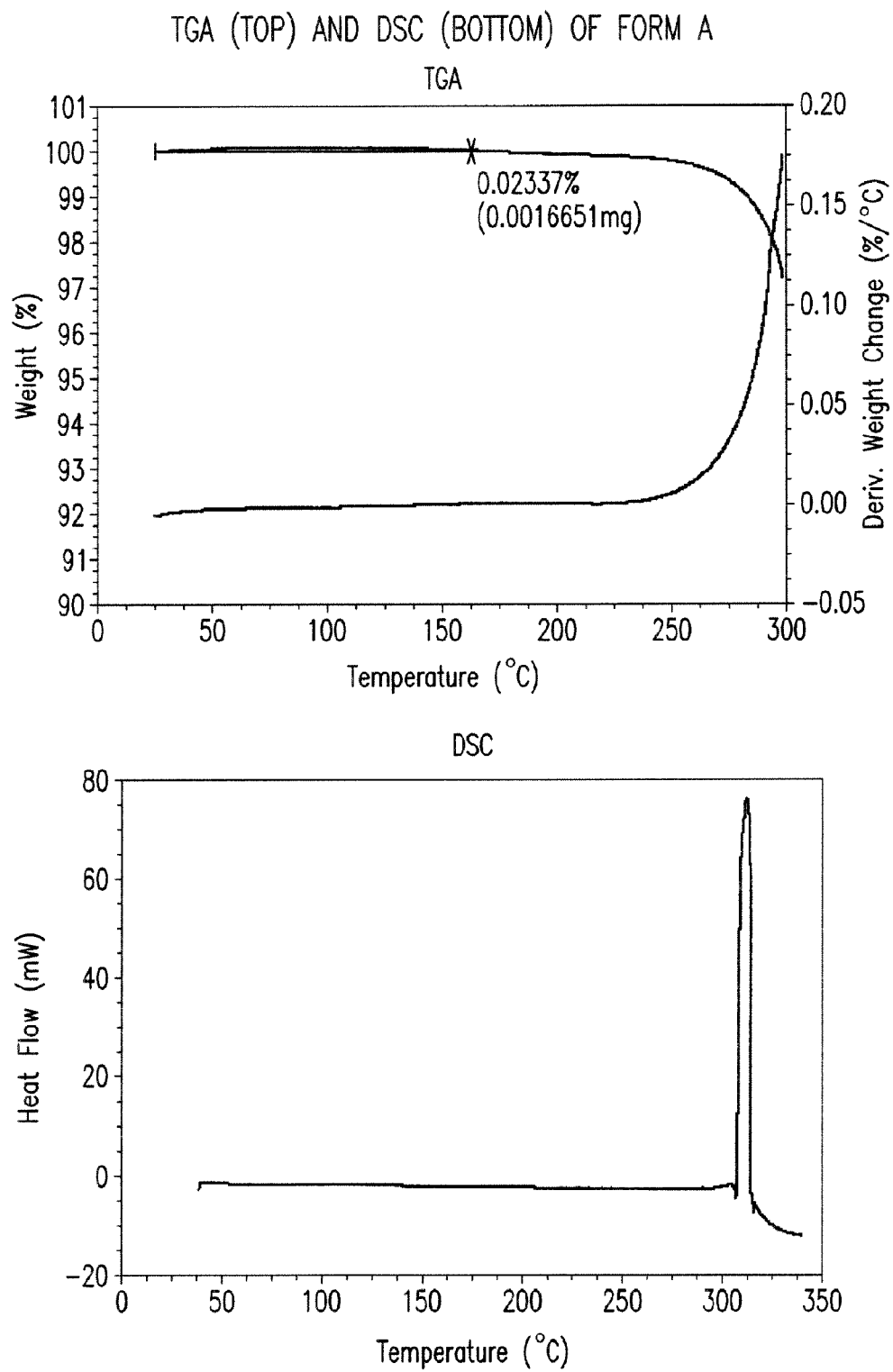
Figure 5:
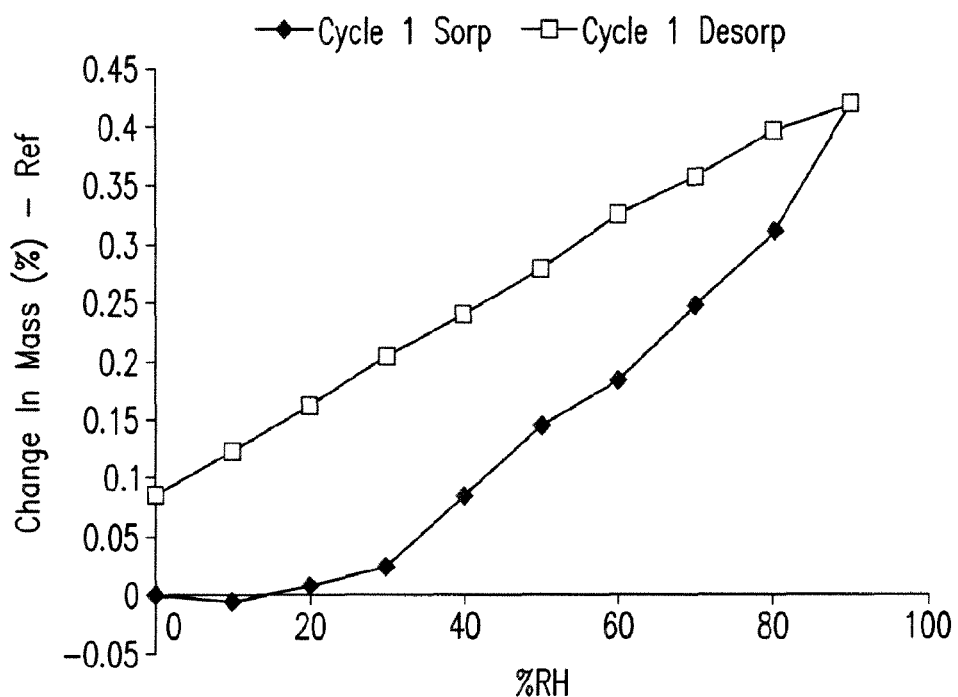
Figure 6:
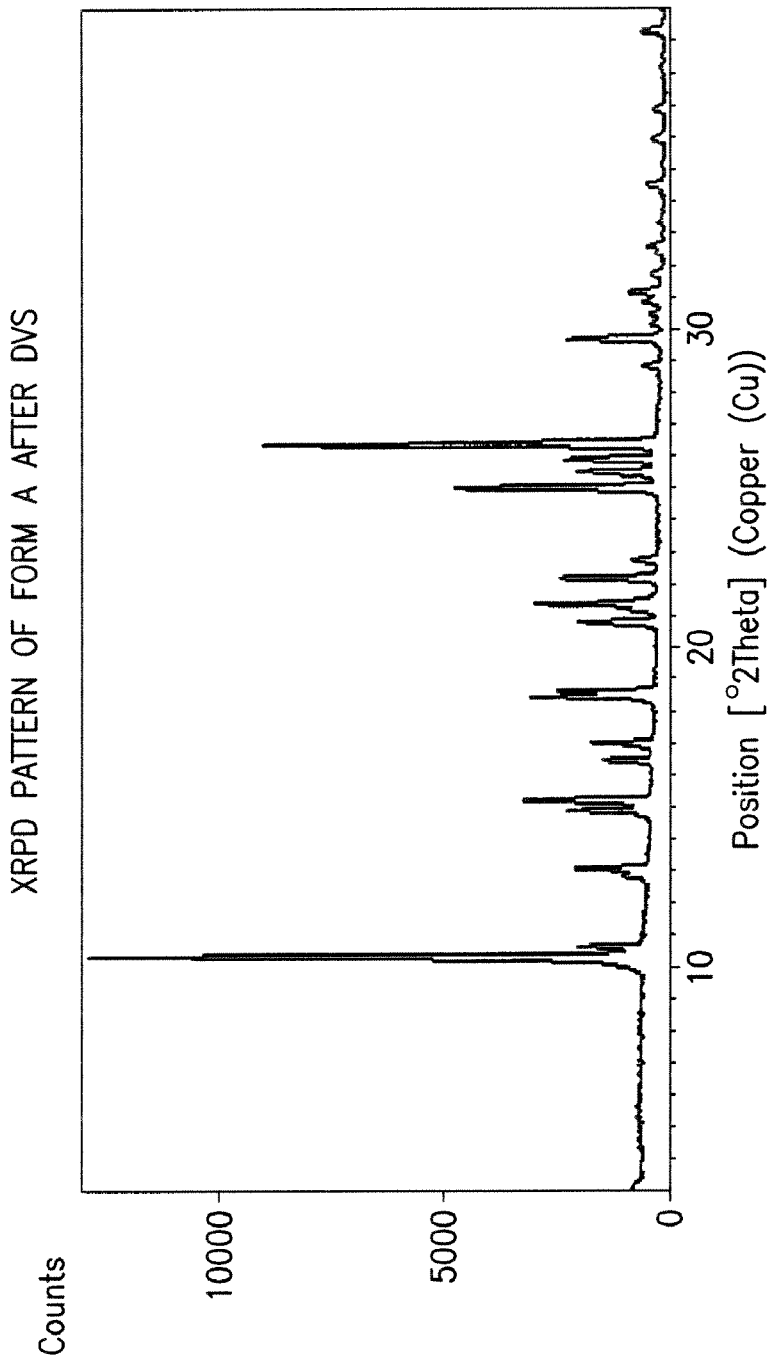
Figure 7:
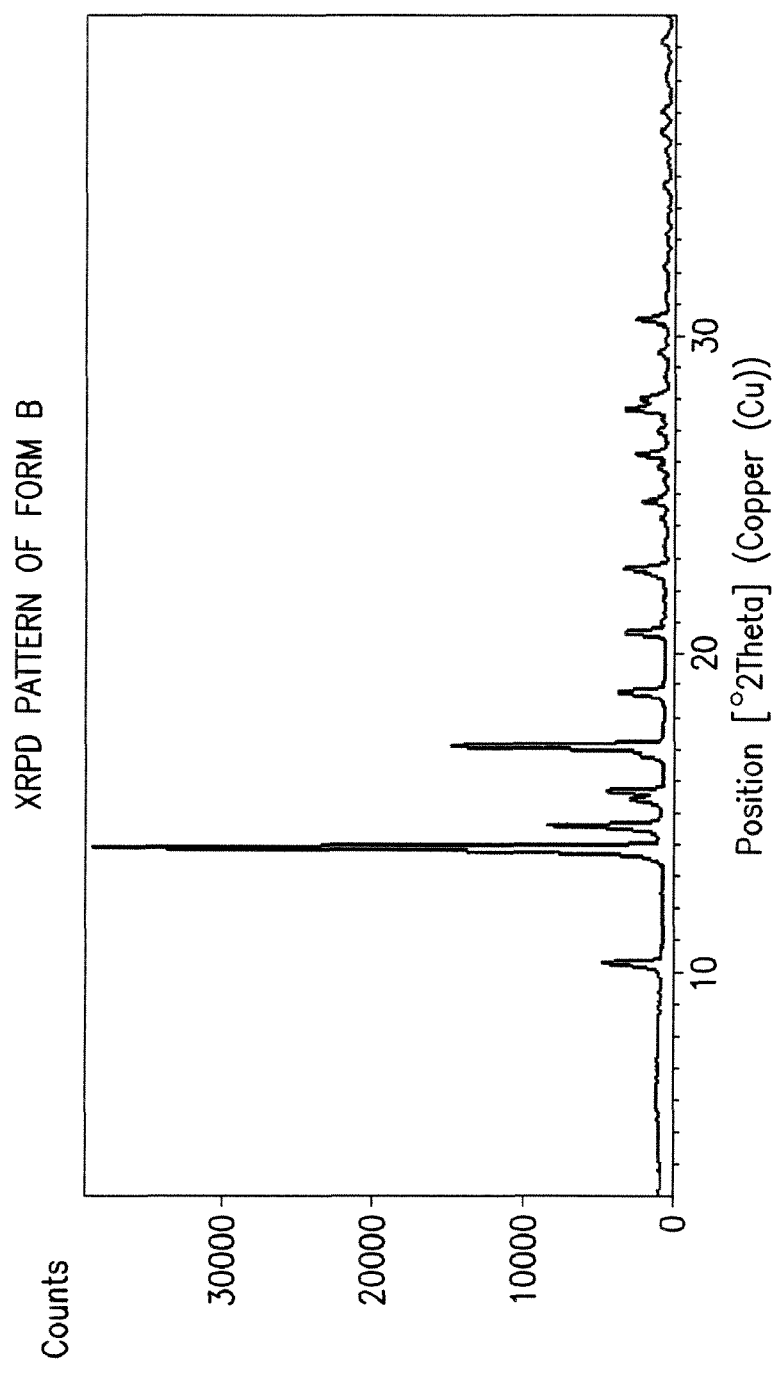
Figure 9:
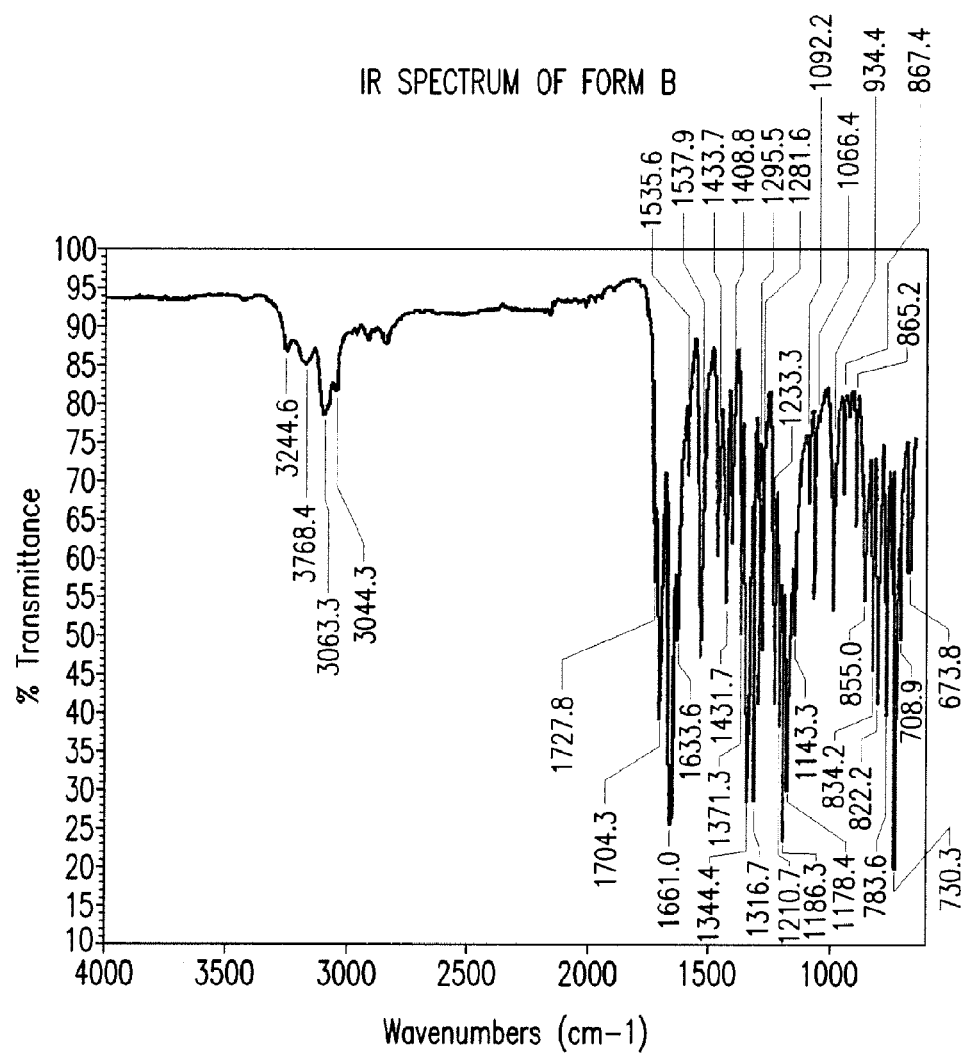
Figure 10:
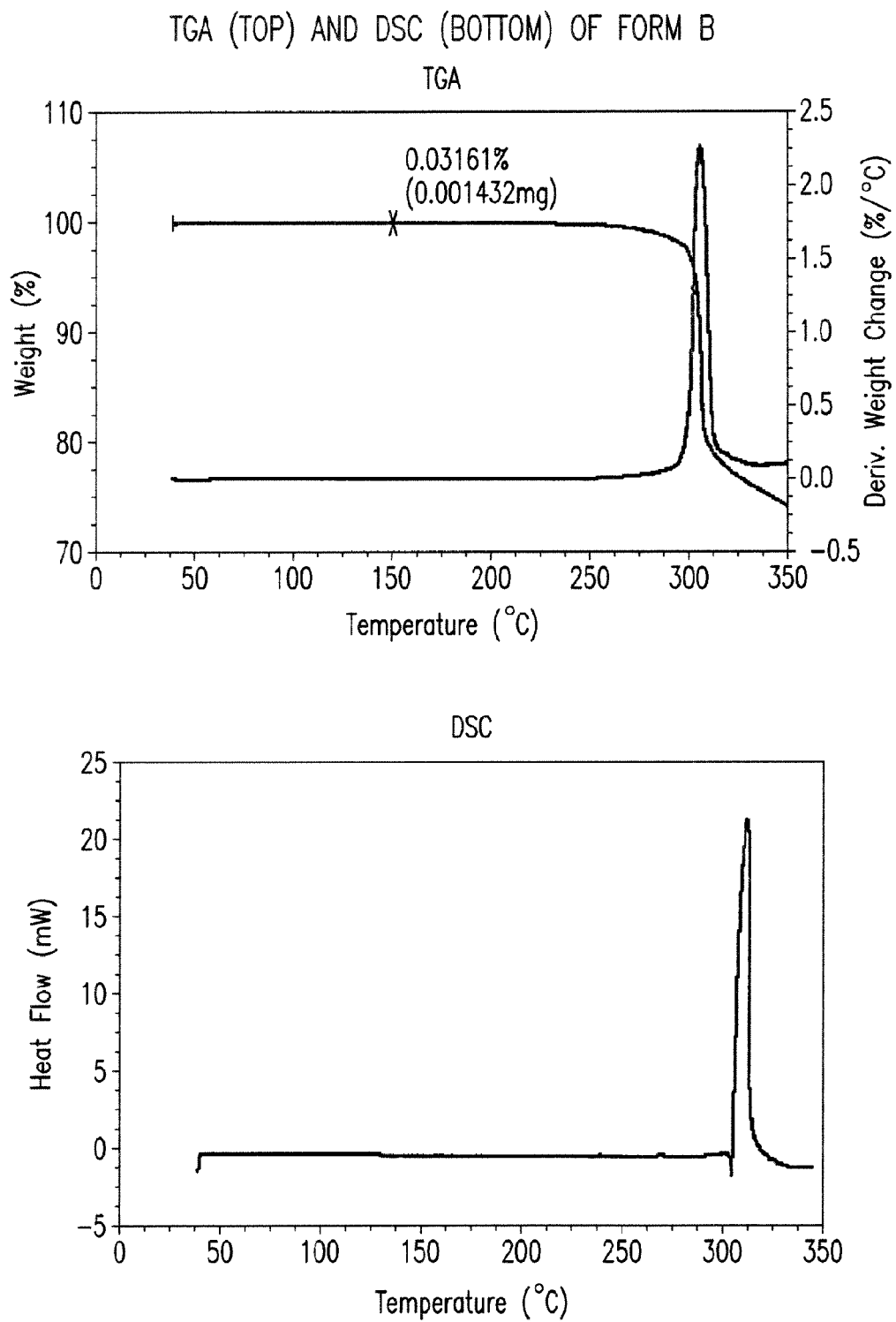
Figure 11:
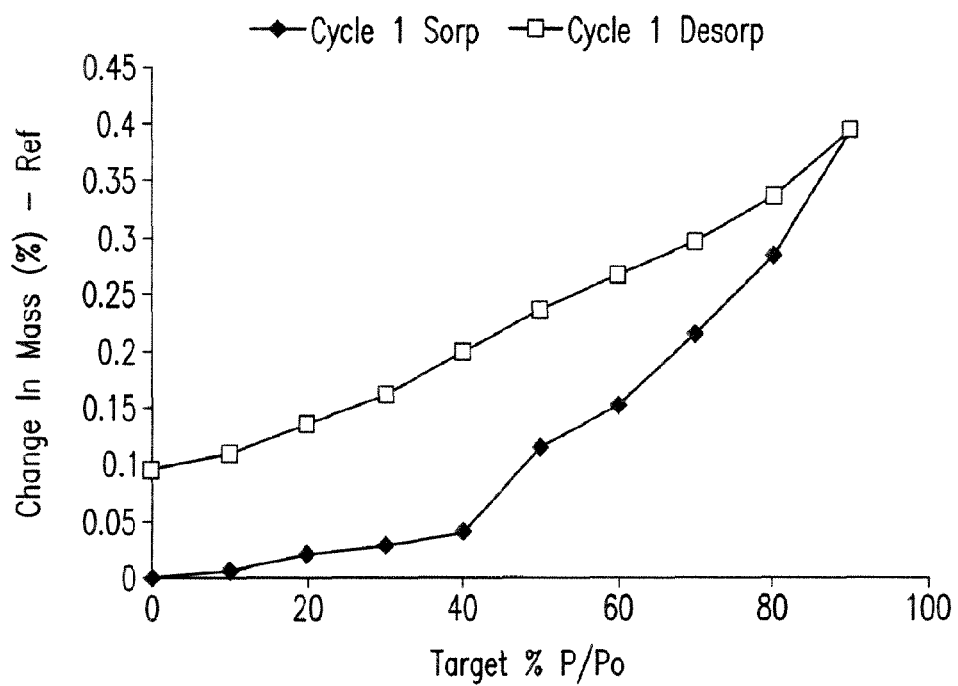
Figure 12:
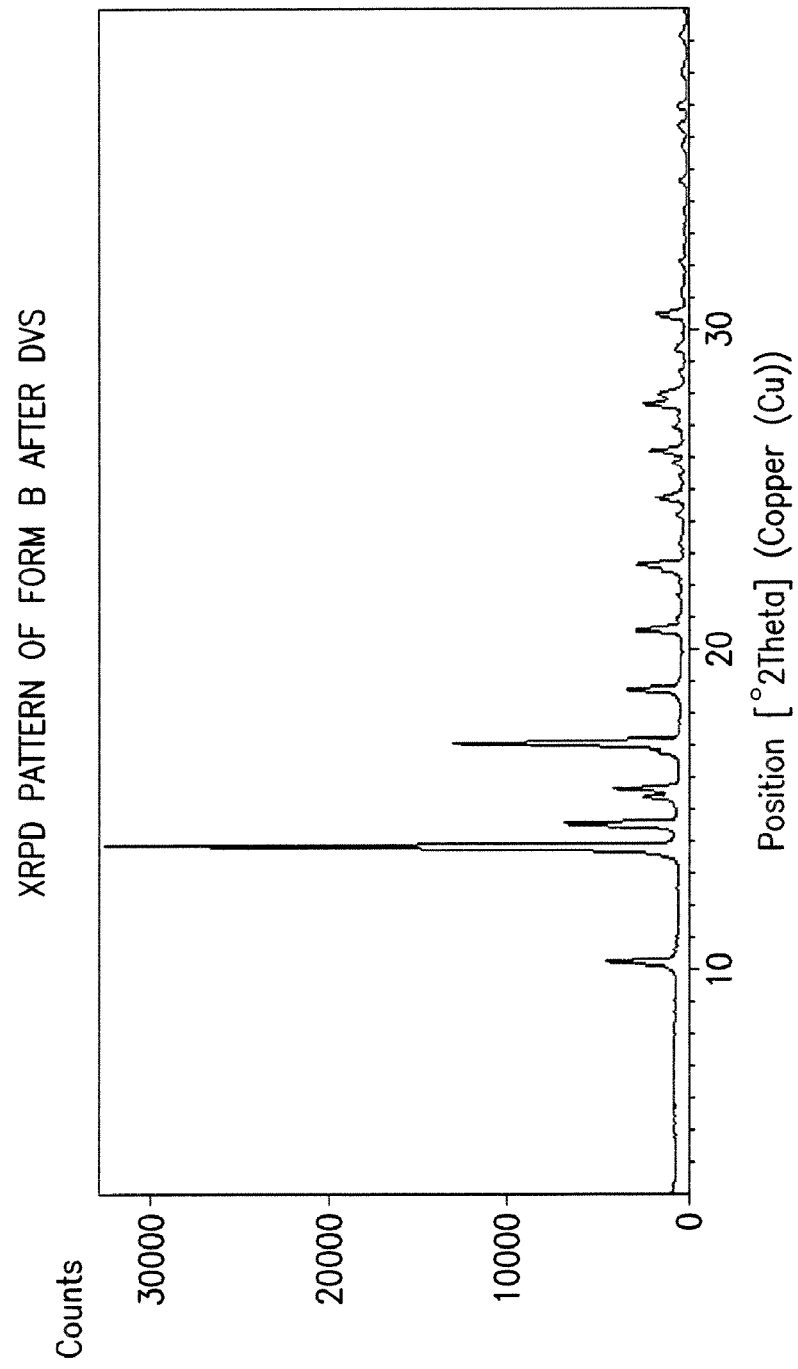
Figure 13:
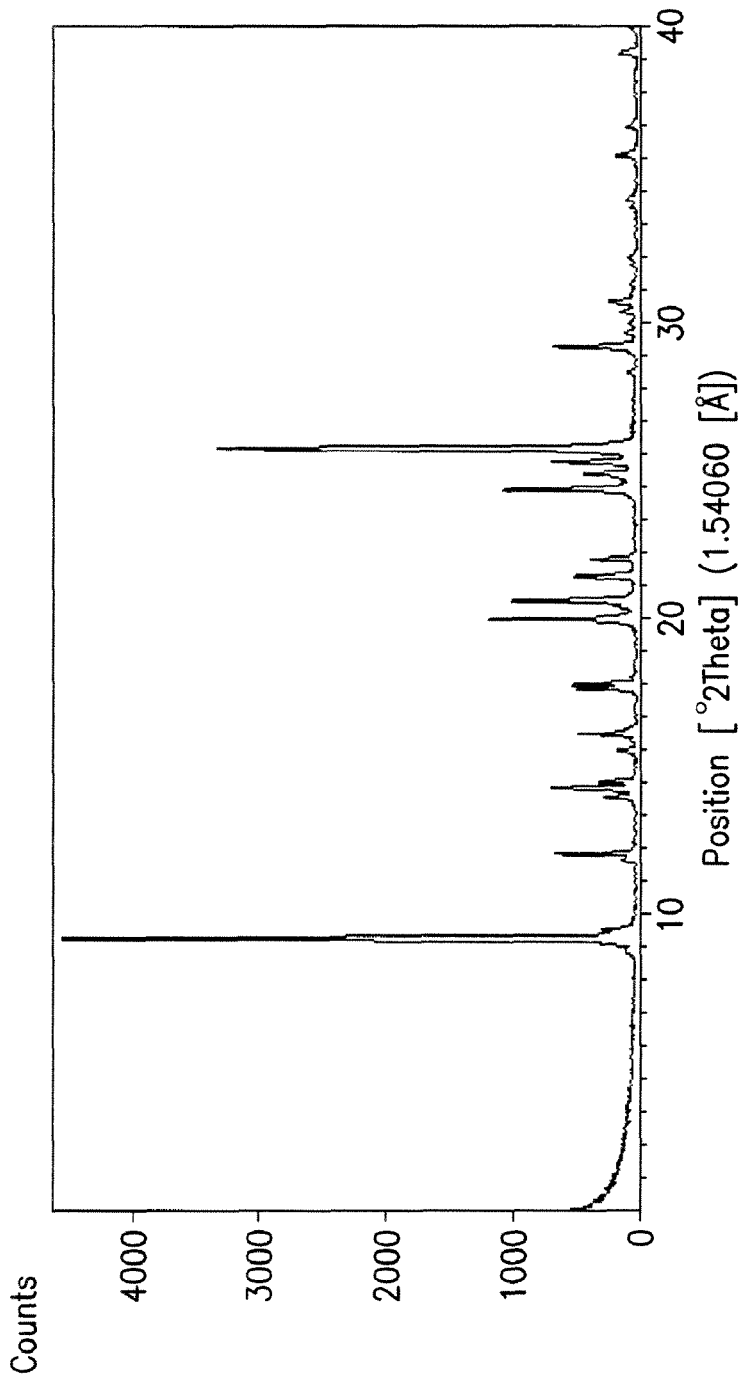
Figure 14:
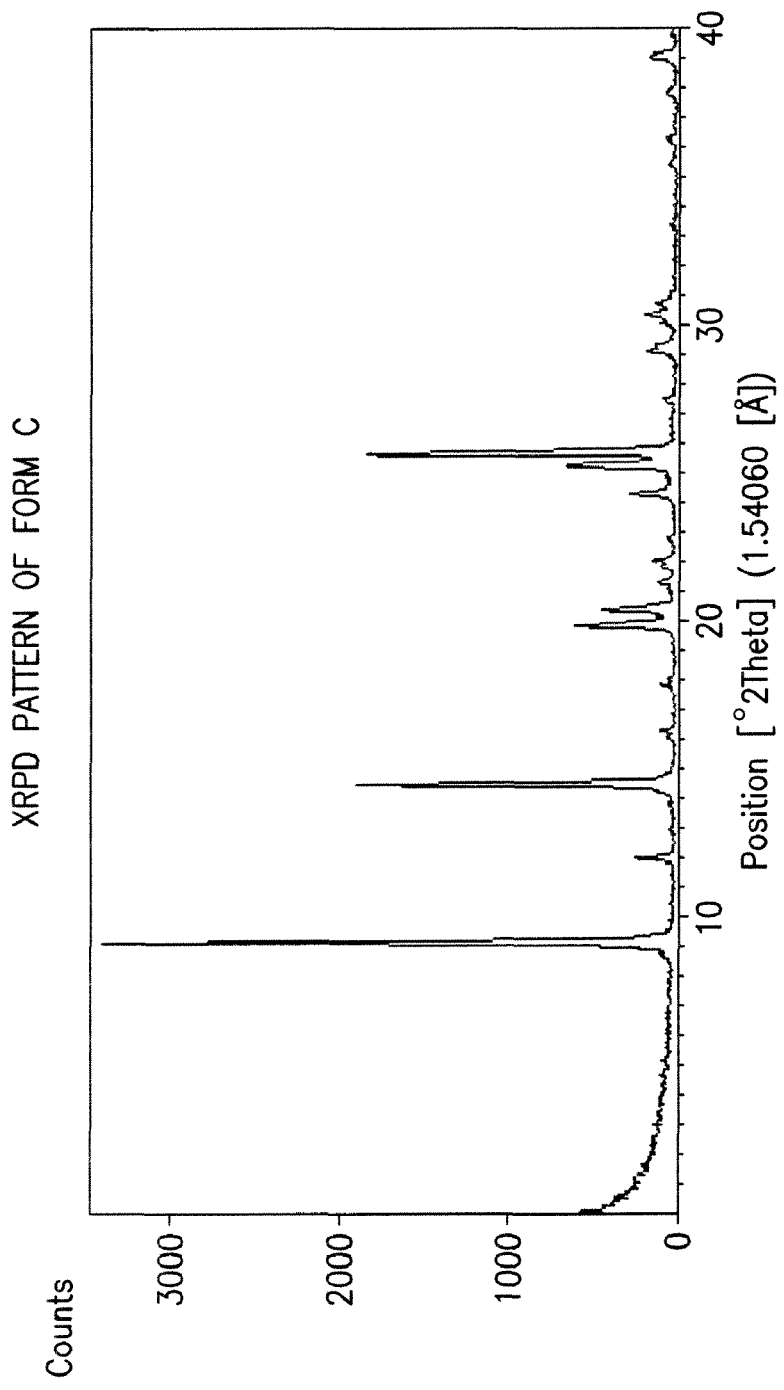
Figure 16:
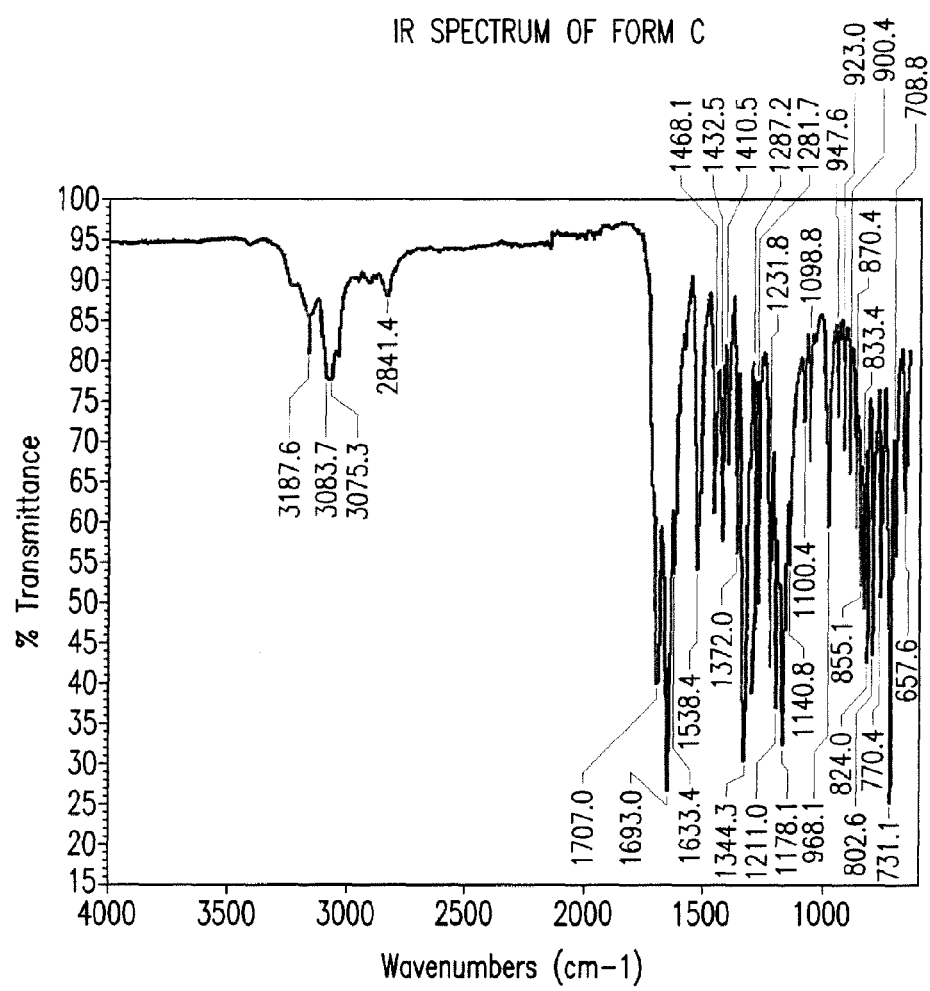
Figure 17:
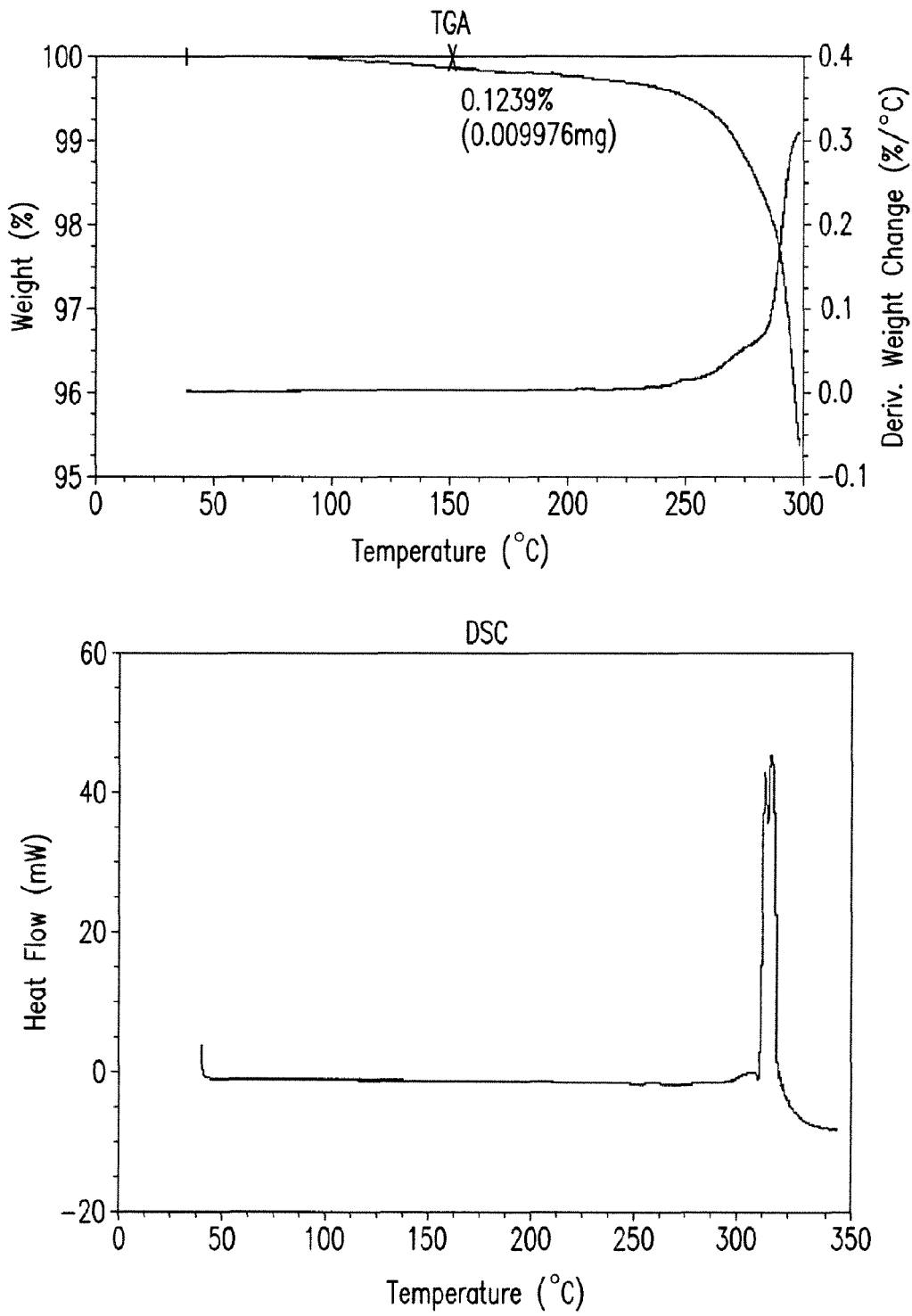
Figure 18:
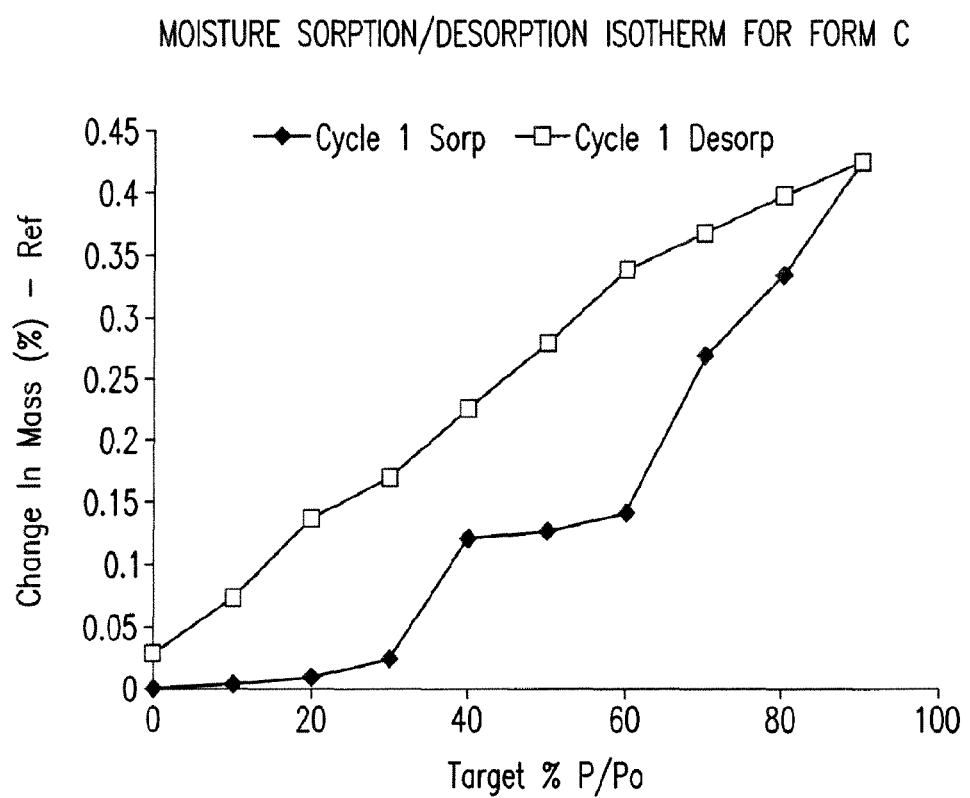
Figure 19:
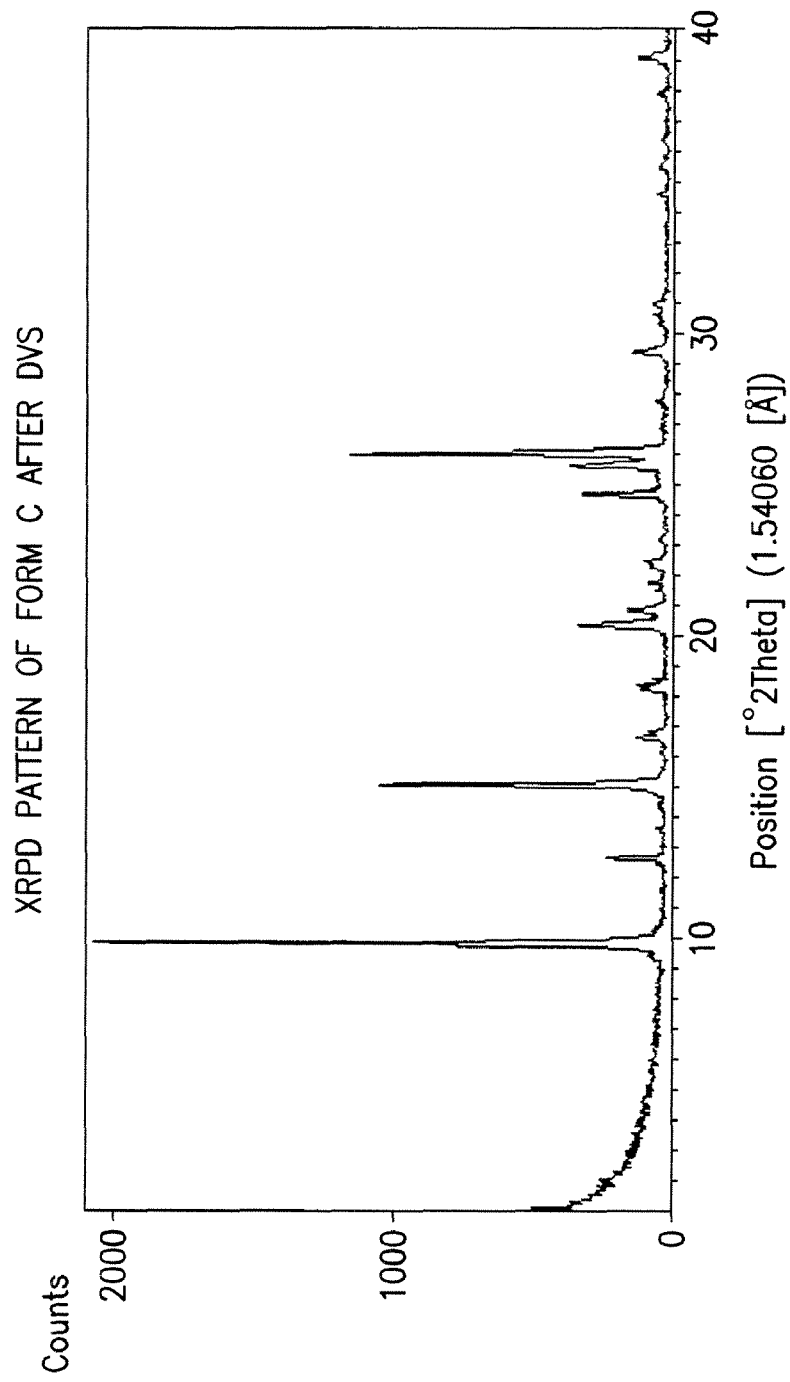
Figure 20:
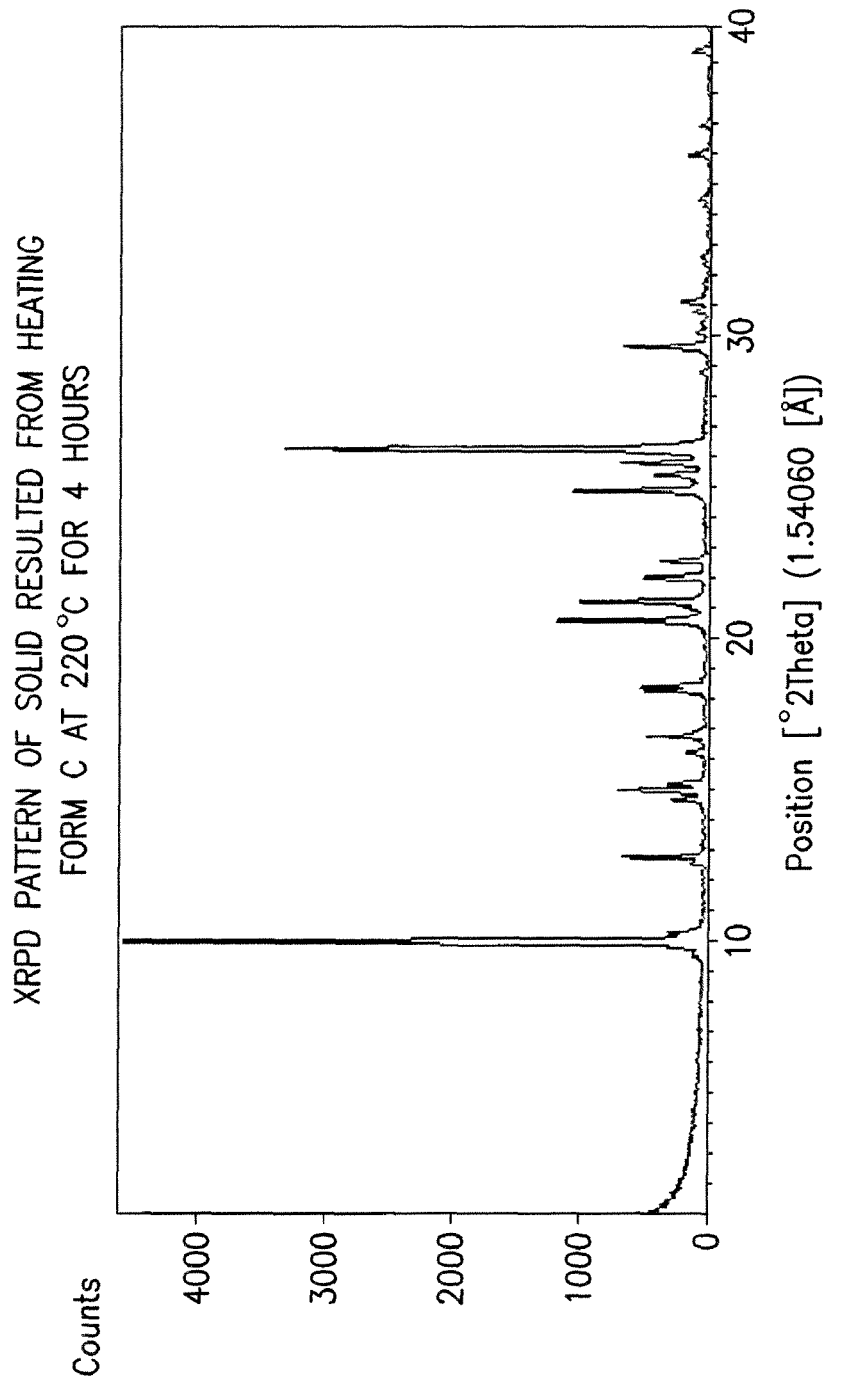

FIG. 1 provides a representative X-ray powder diffraction (XRPD) pattern of Form A;

FIG. 2 provides a representative Miniature Scanning Electron Microscope (Mini SEM) picture of Form A;

FIG. 3 provides a representative IR spectrum of Form A;

FIG. 4 provides a representative thermogravimetric analysis (TGA) curve and a representative differential scanning calorimeter (DSC) thermogram of Form A;

FIG. 5 provides a representative moisture sorption/desorption isotherm of Form A;

FIG. 6 provides a representative X-ray powder diffraction (XRPD) pattern of Form A after Dynamic Vapor Sorption (DVS);

FIG. 7 provides a representative X-ray powder diffraction (XRPD) pattern of Form B;

FIG. 8 provides a representative Miniature Scanning Electron Microscope (Mini SEM) picture of Form B;

FIG. 9 provides a representative IR spectrum of Form B;

FIG. 10 provides a representative thermogravimetric analysis (TGA) curve and a representative differential scanning calorimeter (DSC) thermogram of Form B;

FIG. 11 provides a representative moisture sorption/desorption isotherm of Form B;

FIG. 12 provides a representative X-ray powder diffraction (XRPD) pattern of Form B after Dynamic Vapor Sorption (DVS);

FIG. 13 provides a representative X-ray powder diffraction (XRPD) pattern of solid resulted from heating Form B at 220° C. for 4 hours;

FIG. 14 provides a representative X-ray powder diffraction (XRPD) pattern of Form C;

FIG. 15 provides a representative Miniature Scanning Electron Microscope (Mini SEM) picture of Form C;

FIG. 16 provides a representative IR spectrum of Form C;

FIG. 17 provides a representative thermogravimetric analysis (TGA) curve and a representative differential scanning calorimeter (DSC) thermogram of Form C;

FIG. 18 provides a representative moisture sorption/desorption isotherm of Form C;

FIG. 19 provides a representative X-ray powder diffraction (XRPD) pattern of Form C after Dynamic Vapor Sorption (DVS);

FIG. 20 provides a representative X-ray powder diffraction (XRPD) pattern of solid resulted from heating Form C at 220° C. for 4 hours.

Figure 21:
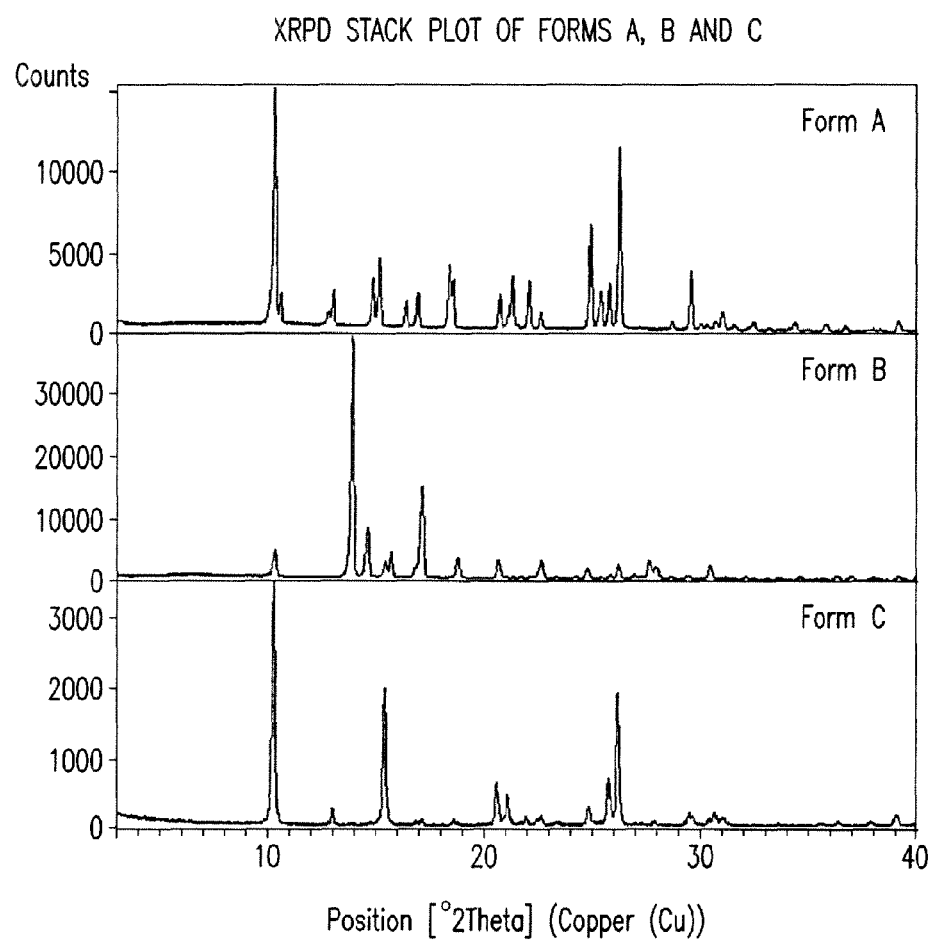

FIG. 21 provides an X-ray powder diffraction (XRPD) stack plot of Forms A, B and C.

Figure 22:
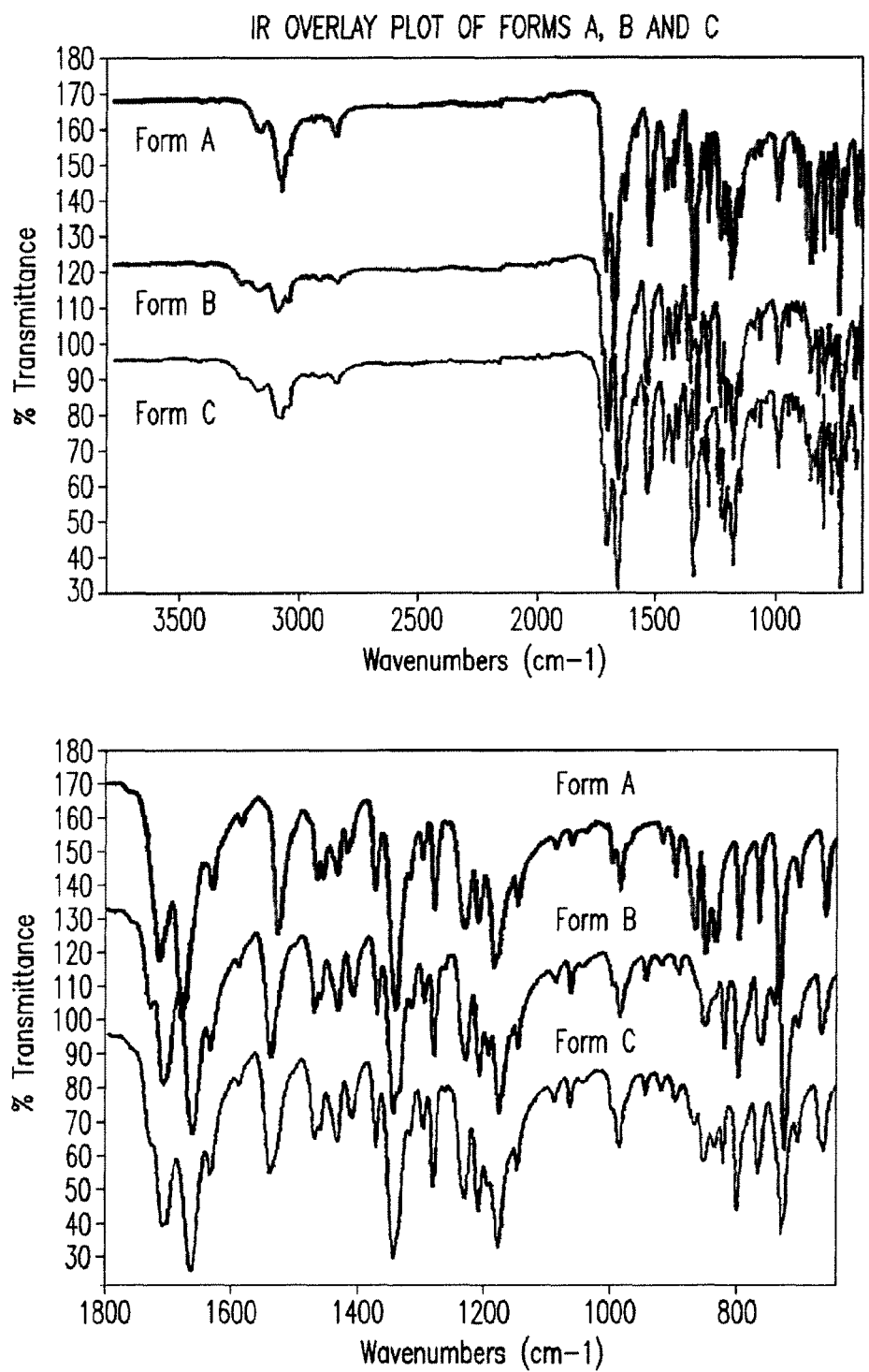

FIG. 22 provides an IR overlay plot of Forms A, B and C.

Figure 23:
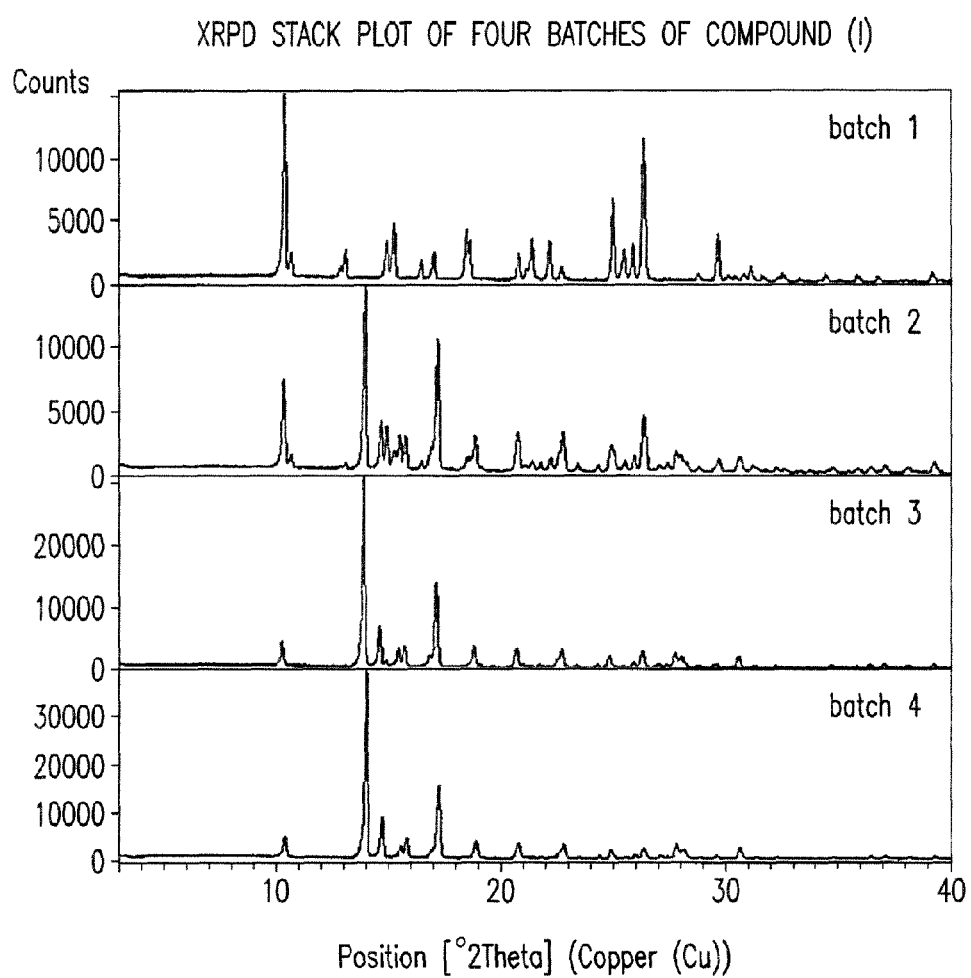

FIG. 23 provides an X-ray powder diffraction (XRPD) stack plot of four batches of Compound (I).

Figure 24:
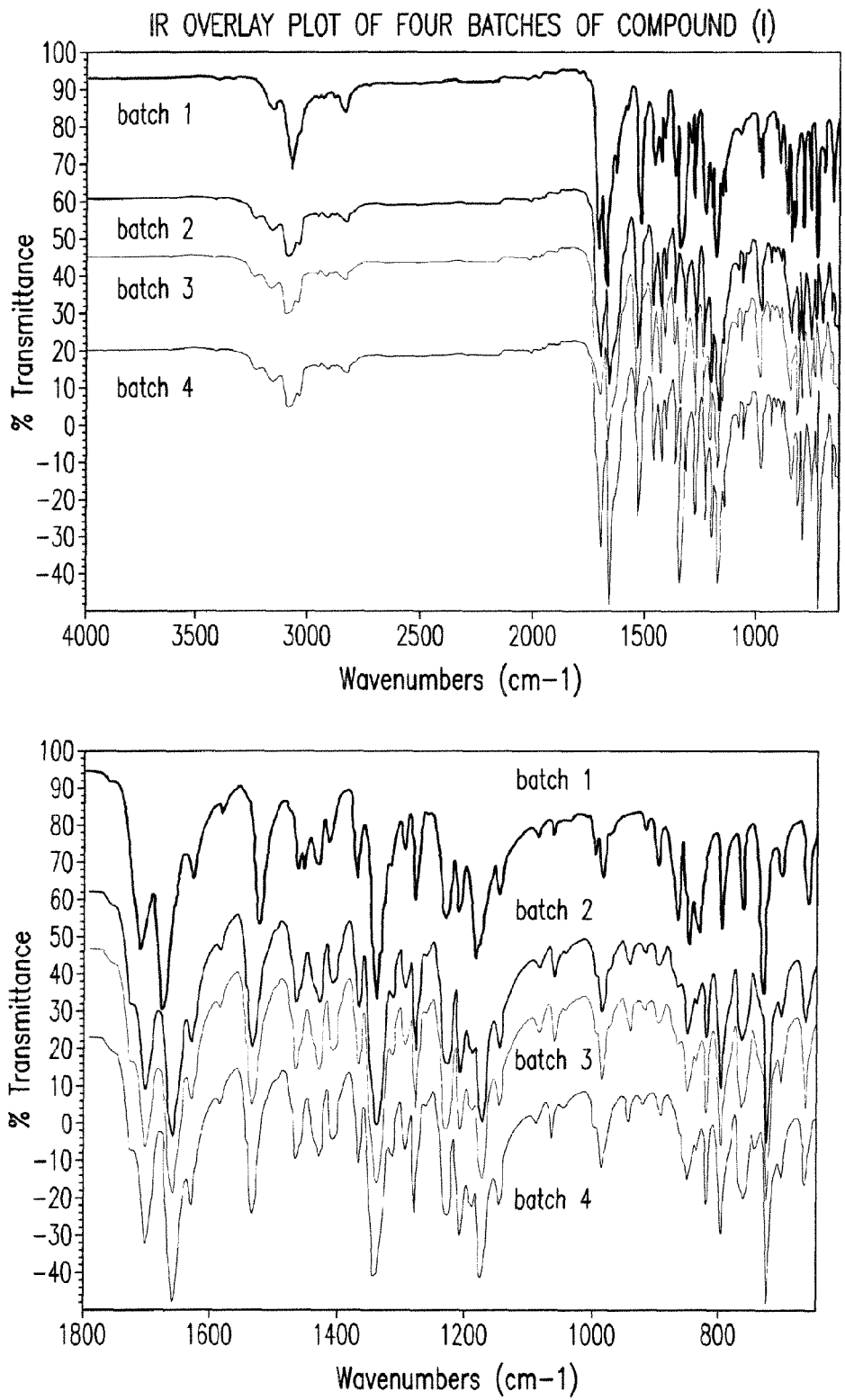

FIG. 24 provides an IR overlay plot of four batches of Compound (I).

5. DETAILED DESCRIPTION

5.1 Definition

As used herein and unless otherwise indicated, the terms "treat," "treating" and "treatment" refer to the alleviation of a disease or disorder and/or at least one of its attendant symptoms.

As used herein and unless otherwise indicated, the terms "prevent," "preventing" and "prevention" refer to the inhibition of a symptom of a disease or disorder or the disease itself.

As used herein and unless otherwise specified, the terms "solid form" and related terms refer to a physical form which is not predominantly in a liquid or a gaseous state. Solid forms may be crystalline, amorphous or mixtures thereof. In particular embodiments, solid forms may be liquid crystals.

A solid form may be a single component or multiple component solid form. A "single-component" solid form comprising a compound consists essentially of the compound. A "multiple-component" solid form comprising a compound comprises a significant quantity of one or more additional species, such as ions and/or molecules, within the solid form. For example, in particular embodiments, a crystalline multiple-component solid form comprising a compound further comprises one or more species non-covalently bonded at regular positions in the crystal lattice.

As used herein and unless otherwise specified, the term "crystalline" and related terms used herein, when used to describe a substance, modification, material, component or product, unless otherwise specified, mean that the substance, modification, material, component or product is substantially crystalline as determined by X-ray diffraction. See, e.g., *Remington: The Science and Practice of Pharmacy*, 21$^{st}$ edition, Lippincott, Williams and Wilkins, Baltimore, Md. (2005); *The United States Pharmacopeia*, 23$^{rd}$ edition, 1843-1844 (1995).

As used herein and unless otherwise specified, the term "crystal forms" and related terms herein refer to solid forms that are crystalline. Crystal forms include single-component crystal forms and multiple-component crystal forms, and include, but are not limited to, polymorphs, solvates, hydrates, and other molecular complexes, as well as salts, solvates of salts, hydrates of salts, other molecular complexes of salts, and polymorphs thereof. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

As used herein and unless otherwise specified, the terms "polymorphs," "polymorphic forms" and related terms herein, refer to two or more crystal forms that consist essentially of the same molecule, molecules or ions. Like different crystal forms, different polymorphs may have different physical properties such as, for example, melting temperatures, heats of fusion, solubilities, dissolution rates and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to a thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (for example, one polymorph might be more likely to form solvates or might be difficult to filter and wash free of impurities, and particle shape and size distribution might be different between polymorphs).

Polymorphs of a molecule can be obtained by a number of methods known in the art. Such methods include, but are not limited to, melt recrystallization, melt cooling, solvent recrystallization, desolvation, rapid evaporation, rapid cooling, slow cooling, vapor diffusion and sublimation. Polymorphs can be detected, identified, classified and characterized using well-known techniques such as, but not limited to, differential scanning calorimetry (DSC), thermogravimetry (TGA), X-ray powder diffractometry (XRPD), single crystal X-ray diffractometry, vibrational spectroscopy, solution calorimetry, solid state nuclear magnetic resonance (NMR), infrared (IR) spectroscopy, Raman spectroscopy, hot stage optical microscopy, scanning electron microscopy (SEM), electron crystallography and quantitative analysis, particle size analysis (PSA), surface area analysis, solubility, and rate of dissolution.

As used herein to refer to the spectra or data presented in graphical form (e.g., XRPD, IR, Raman and NMR spectra), and unless otherwise indicated, the term "peak" refers to a peak or other special feature that one skilled in the art would recognize as not attributable to background noise. The term "significant peaks" refers to peaks at least the median size (e.g., height) of other peaks in the spectrum or data, or at least 1.5, 2, or 2.5 times the median size of other peaks in the spectrum or data.

As used herein and unless otherwise indicated, the term "substantially pure" when used to describe a polymorph of a compound means a solid form of the compound that comprises that polymorph and is substantially free of other polymorphs of the compound. A representative substantially pure polymorph comprises greater than about 80% by weight of one polymorphic form of the compound and less than about 20% by weight of other polymorphic forms of the compound, more preferably greater than about 90% by weight of one polymorphic form of the compound and less than about 10% by weight of the other polymorphic forms of the compound, even more preferably greater than about 95% by weight of one polymorphic form of the compound and less than about 5% by weight of the other polymorphic forms of the compound, and most preferably greater than about 97% by weight of one polymorphic forms of the compound and less than about 3% by weight of the other polymorphic forms of the compound.

The term "substantially similar," when used herein in the context of comparing spectra such as, but not limited to, X-ray powder diffraction pattern or differential scanning calorimetry scan obtained for a solid form, means that two spectra share defining characteristics sufficient to differentiate them from a spectrum obtained for a different solid form. In certain embodiments, the term "substantially similar" means that two spectra are the same, i.e., visibly overlap. In certain embodiments, spectra or characterization data that are substantially similar to those of a reference crystalline form, amorphous form, or mixture thereof, is understood by those of ordinary skill in the art to correspond to the same crystalline form, amorphous form, or mixture thereof as the particular reference. In analyzing whether spectra or characterization data are substantially similar, a person of ordinary skill in the art understands that particular characterization data points may vary to a reasonable extent while still describing a given solid form, due to, for example, experimental error and routine sample-to-sample analysis.

5.2 Solid Forms

In some embodiments, provided herein are solid forms comprising crystalline 3-(4-nitro-1-oxoisoindolin-2-yl)piperidine-2,6-dione, which is a compound of Formula (I)

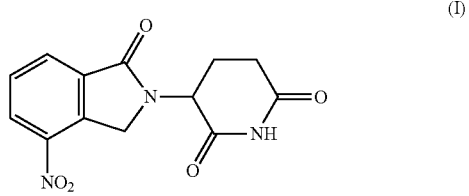 [SMILES: O=C1CCC(N2Cc3c(cccc3[N+](=O)[O-])C2=O)C(=O)N1]

(I)

This compound can be prepared according to the methods described in U.S. Pat. Nos. 6,281,230 and 5,635,517, the entireties of which are incorporated herein by reference. For example, the compound can be prepared by allowing 2,6-dioxopiperidin-3-ammonium chloride to react with methyl 2-bromomethyl-3-nitrobenzoate in dimethylformamide in the presence of triethylamine. The methyl 2-bromomethyl-3-nitrobenzoate in turn is obtained from the corresponding methyl ester of 3-nitro-ortho-toluic acid by conventional bromination with N-bromosuccinimide under the influence of light. The compound can be used for the preparation of 3-(4-amino-1-oxoisoindolin-2-yl)piperidine-2,6-dione through catalytic hydrogenation.

Polymorphs of 3-(4-nitro-1-oxoisoindolin-2-yl)piperidine-2,6-dione can be obtained by techniques known in the art, including solvent recrystallization, desolvation, vapor diffusion, rapid evaporation, slow evaporation, rapid cooling and slow cooling. Polymorphs can be made by dissolving a weighed quantity of 3-(4-nitro-1-oxoisoindolin-2-yl)piperidine-2,6-dione in various solvents at elevated temperatures. The solutions of the compound can then be filtered and allowed to evaporate either in an open vial (for fast hot evaporation) or in a vial covered with aluminum foil containing pinholes (hot slow evaporation). Polymorphs can also be obtained from slurries. Polymorphs can be crystallized from solutions or slurries using several methods. For example, a solution created at an elevated temperature (e.g., 60° C.) can be filtered quickly then allowed to cool to room temperature. Once at room temperature, the sample that did not crystallize can be moved to a refrigerator then filtered. Alternatively, the solutions can be crash cooled by dissolving the solid in a solvent at an increased temperature (e.g., 45-65° C.) followed by cooling in a dry ice/solvent bath.

In one embodiment, provided herein is Form A of 3-(4-nitro-1-oxoisoindolin-2-yl)piperidine-2,6-dione. Form A is an anhydrate, crystalline material. In another embodiment, provided herein is Form B of 3-(4-nitro-1-oxoisoindolin-2-yl)piperidine-2,6-dione. Form B is an anhydrate, crystalline material that is monotropically related to Form A. In yet another embodiment, provided herein is Form C of 3-(4-nitro-1-oxoisoindolin-2-yl)piperidine-2,6-dione. Form C is an anhydrate, crystalline material that is monotropically related to Form A. Each of these forms is discussed in detail below.

In one embodiment, provided herein is a composition comprising amorphous 3-(4-nitro-1-oxoisoindolin-2-yl)piperidine-2,6-dione and crystalline 3-(4-nitro-1-oxoisoindolin-2-yl)piperidine-2,6-dione of form A, B and C. Specific compositions can comprise greater than 50, 75, 90 or 95 weight percent crystalline 3-(4-nitro-1-oxoisoindolin-2-yl) piperidine-2,6-dione.

In another embodiment, provided herein is a composition comprising at least two crystalline forms of 3-(4-nitro-1-oxoisoindolin-2-yl)piperidine-2,6-dione (e.g., a mixture of polymorph forms A and C).

5.2.1 Form A

Form A can be obtained using the experimental methods described in Example 6.1, provided below.

A representative XRPD pattern of Form A is provided in FIG. 1. In certain embodiments, Form A of Compound (I) is characterized by XRPD peaks, preferably significant peaks, located at, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, or all of the following approximate positions: 10.30, 10.59, 12.80, 13.03, 14.85, 15.15, 16.40, 16.93, 18.39, 18.55, 20.71, 21.08, 21.28, 21.53, 22.08, 22.63, 24.91, 25.40, 25.78, 26.25, 28.70, 29.55, 30.02, 30.31, 30.69, 31.00, 31.56, 32.43, 33.17, 34.34, 35.78, 36.68, and 39.12 degrees 2θ, plus or minus 0.10. In some embodiments, Form A has at least 8, at least 9, or at least 10 peaks. In some embodiments, Form A has at least 10 peaks.

In certain embodiments, Form A is characterized by peaks in an XRPD pattern located at 1, 2, 3, 4, 5, 6, or all of the following approximate peak positions: 10.30±0.10, 15.15±0.10, 18.39±0.10, 21.28±0.10, 24.91±0.10, 26.25±0.10, and 29.55±0.10 degrees 2θ. In certain embodiments, Form A is characterized by two or more peaks selected from 10.30±0.10, 15.15±0.10, 18.39±0.10, 21.28±0.10, 24.91±0.10, 26.25±0.10, and 29.55±0.10 degrees 2θ. In certain embodiments, Form A is characterized by three or more peaks selected from 10.30±0.10, 15.15±0.10, 18.39±0.10, 21.28±0.10, 24.91±0.10, 26.25±0.10, and 29.55±0.10 degrees 2θ. In certain embodiments, Form A is characterized by four or more peaks selected from 10.30±0.10, 15.15±0.10, 18.39±0.10, 21.28±0.10, 24.91±0.10, 26.25±0.10, and 29.55±0.10 degrees 2θ. In certain embodiments, Form A is characterized by five or more peaks selected from 10.30±0.10, 15.15±0.10, 18.39±0.10, 21.28±0.10, 24.91±0.10, 26.25±0.10, and 29.55±0.10 degrees 2θ. In certain embodiments, Form A is characterized by six or more peaks selected from 10.30±0.10, 15.15±0.10, 18.39±0.10, 21.28±0.10, 24.91±0.10, 26.25±0.10, and 29.55±0.10 degrees 2θ. In certain embodiments, Form A is characterized by all of the following peaks: 10.30±0.10, 15.15±0.10, 18.39±0.10, 21.28±0.10, 24.91±0.10, 26.25±0.10, and 29.55±0.10 degrees 2θ. In certain embodiments, Form A is characterized by an XRPD pattern substantially similar to the XRPD pattern presented in FIG. 1.

In certain embodiments, provided herein is a solid form of Compound (I) having an XRPD pattern comprising peaks at approximately 10.30, 24.91, and 26.25 degrees 2θ. In further embodiments, the XRPD pattern further comprises peaks at approximately 15.15, 18.39, 21.28, and 29.55 degrees 2θ. In even further embodiments, the XRPD pattern further comprises peaks at approximately 10.59, 13.03, 14.85, 16.40, 16.93, 18.55, 20.71, 22.08, 22.63, 25.40, and 25.78 degrees 2θ.

In some embodiments, the XRPD peaks above (degrees 2θ peaks) are when analyzed using copper Kα radiation. In some embodiments, provided herein is a solid form of Compound (I), which has an XRPD pattern comprising peaks at approximately 10.30, 24.91, and 26.25 degrees 2θ when analyzed using copper Kα radiation.

Form A has an irregular rod habit as shown in FIG. 2. Representative IR spectrum data of Form A is provided in FIG. 3. In certain embodiments, provided herein is a solid form of Compound (I), wherein the solid form is characterized by an IR spectrum substantially similar to the IR spectrum presented in FIG. 3.

Representative thermal characteristics of Form A are shown in FIG. 4. The TGA data shows minimal weight loss up to about 160° C. In certain embodiments, provided herein is a solid form of Compound (I), wherein the solid form is characterized by a TGA thermogram substantially similar to the TGA thermogram presented in FIG. 4. The DSC thermogram shows only one major event at slightly above 300° C. These data indicate that Form A is an anhydrate. In certain embodiments, the temperature maximum at slightly above 300° C. corresponds to decomposition of Compound (I). In certain embodiments, provided herein is a solid form of Compound (I), wherein the solid form is characterized by a DSC thermogram substantially similar to the DSC thermogram presented in FIG. 4.

Representative moisture sorption and desorption data of Form A are plotted in FIG. 5. In certain embodiments, form A exhibits a total mass change of 0.42% between 0% and 90% relative humidity, suggesting Form A is not hygroscopic. In certain embodiments, provided herein is a solid form of Compound (I), wherein the solid form is characterized by a DVS plot substantially similar to the DVS plot presented in FIG. 5. After undergoing the adsorption/desorption cycles, the XRPD pattern of Form A shows no change, as shown in FIG. 6. In certain embodiments, Form A is characterized by an XRPD pattern substantially similar to the XRPD pattern presented in FIG. 6.

Form conversion studies show that Form A appears to be the most thermodynamically stable form of 3-(4-nitro-1-oxoisoindolin-2-yl)piperidine-2,6-dione discovered thus far, and no conversion from Form A to other forms has been observed.

All of the combinations of the above embodiments are encompassed by this invention.

5.2.2 Form B

Form B can be obtained using the experimental methods described in Example 6.1, provided below.

A representative XRPD pattern of Form B is provided in FIG. 7. In certain embodiments, Form B of Compound (I) is characterized by XRPD peaks, preferably significant peaks, located at, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the following approximate positions: 10.32, 13.94, 14.63, 15.46, 15.72, 16.83, 17.14, 18.82, 20.68, 22.48, 22.69, 24.27, 24.79, 25.86, 26.26, 26.99, 27.33, 27.69, 28.01, 29.45, 30.49, 30.56, 34.64, 36.33, 36.97, and 39.15 degrees 2θ, plus or minus 0.10. In some embodiments, Form B has at least 8, at least 9, or at least 10 peaks. In some embodiments, Form B has at least 10 peaks.

In certain embodiments, Form B is characterized by peaks in an XRPD pattern located at 1, 2, 3, 4, 5, 6, 7, 8, or all of the following approximate peak positions: 10.32±0.10, 13.94±0.10, 14.63±0.10, 15.72±0.10, 17.14±0.10, 18.82±0.10, 20.68±0.10, 22.69±0.10, and 27.69±0.10 degrees 2θ. In certain embodiments, Form B is characterized by two or more peaks selected from 10.32±0.10, 13.94±0.10, 14.63±0.10, 15.72±0.10, 17.14±0.10, 18.82±0.10, 20.68±0.10, 22.69±0.10, and 27.69±0.10 degrees 2θ. In certain embodiments, Form B is characterized by three or more peaks selected from 10.32±0.10, 13.94±0.10, 14.63±0.10, 15.72±0.10, 17.14±0.10, 18.82±0.10, 20.68±0.10, 22.69±0.10, and 27.69±0.10 degrees 2θ. In certain embodiments, Form B is characterized by four or more peaks selected from 10.32±0.10, 13.94±0.10, 14.63±0.10, 15.72±0.10, 17.14±0.10, 18.82±0.10, 20.68±0.10, 22.69±0.10, and 27.69±0.10 degrees 2θ. In certain embodiments, Form B is characterized by five or more peaks selected from 10.32±0.10, 13.94±0.10, 14.63±0.10, 15.72±0.10, 17.14±0.10, 18.82±0.10, 20.68±0.10, 22.69±0.10, and 27.69±0.10 degrees 2θ. In certain embodiments, Form B is characterized by six or more peaks selected from 10.32±0.10, 13.94±0.10, 14.63±0.10, 15.72±0.10, 17.14±0.10, 18.82±0.10, 20.68±0.10, 22.69±0.10, and 27.69±0.10 degrees 2θ. In certain embodiments, Form B is characterized by seven or more peaks selected from 10.32±0.10, 13.94±0.10, 14.63±0.10, 15.72±0.10, 17.14±0.10, 18.82±0.10, 20.68±0.10, 22.69±0.10, and 27.69±0.10 degrees 2θ. In certain embodiments, Form B is characterized by eight or more peaks selected from 10.32±0.10, 13.94±0.10, 14.63±0.10, 15.72±0.10, 17.14±0.10, 18.82±0.10, 20.68±0.10, 22.69±0.10, and 27.69±0.10 degrees 20. In certain embodiments, Form B is characterized by all of the following peaks: 10.32±0.10, 13.94±0.10, 14.63±0.10, 15.72±0.10, 17.14±0.10, 18.82±0.10, 20.68±0.10, 22.69±0.10, and 27.69±0.10 degrees 2θ. In certain embodiments, Form B is characterized by an XRPD pattern substantially similar to the XRPD pattern presented in FIG. 7.

In certain embodiments, provided herein is a solid form of Compound (I) having an XRPD pattern comprising peaks at approximately 13.94, 14.63, and 17.14 degrees 2θ. In further embodiments, the XRPD pattern further comprises peaks at approximately 10.32, 15.72, 18.82, 20.68, 22.69, and 27.69 degrees 2θ.

In some embodiments, the XRPD peaks above (degrees 2θ peaks) are when analyzed using copper Kα radiation. In some embodiments, provided herein is a solid form of Compound (I), which has an XRPD pattern comprising peaks at approximately 13.94, 14.63, and 17.14 degrees 2θ when analyzed using copper Kα radiation.

Form B has an irregular rod habit as shown in FIG. 8. Representative IR spectrum data of Form B is provided in FIG. 9. In certain embodiments, provided herein is a solid form of Compound (I), wherein the solid form is characterized by an IR spectrum substantially similar to the IR spectrum presented in FIG. 9.

Representative thermal characteristics of Form B are shown in FIG. 10. The TGA data shows minimal weight loss up to about 150° C. In certain embodiments, provided herein is a solid form of Compound (I), wherein the solid form is characterized by a TGA thermogram substantially similar to the TGA thermogram presented in FIG. 10. The DSC thermogram shows only one major event at slightly above 300° C. These data indicate that Form B is an anhydrate. In certain embodiments, the temperature maximum at slightly above 300° C. corresponds to decomposition of Compound (I). In certain embodiments, provided herein is a solid form of Compound (I), wherein the solid form is characterized by a DSC thermogram substantially similar to the DSC thermogram presented in FIG. 10.

Representative moisture sorption and desorption data of Form B are plotted in FIG. 11. In certain embodiments, form B exhibits a total mass change of 0.39% between 0% and 90% relative humidity, suggesting Form B is not hygroscopic. In certain embodiments, provided herein is a solid form of Compound (I), wherein the solid form is characterized by a DVS plot substantially similar to the DVS plot presented in FIG. 11. After undergoing the adsorption/desorption cycles, the XRPD pattern of Form B shows no change, as shown in FIG. 12. In certain embodiments, Form B is characterized by an XRPD pattern substantially similar to the XRPD pattern presented in FIG. 12.

Form conversion studies show that Form B typically converts to Form A in acetonitrile at 80° C., in acetonitrile/water (2:1) at 60° C., and in acetonitrile/water (1:1) at ambient temperature. Form B also converts to Form A at ambient temperature in other solvent systems such as acetone, water, acetone/water (1:1), and acetonitrile/water/acetone (1:1:1). Form B also converts to Form A upon heating up to 220° C. for 4 hours, which is evidenced by the XRPD pattern of the resulting solid, as shown in FIG. 13. These observations suggest that Form B is monotropically related to Form A. In certain embodiments, Form A is characterized by an XRPD pattern substantially similar to the XRPD pattern presented in FIG. 13.

All of the combinations of the above embodiments are encompassed by this invention.

5.2.3 Form C

Form C can be obtained from recrystallization of 3-(4-nitro-1-oxoisoindolin-2-yl)piperidine-2,6-dione, using 1-methyl-2-pyrrolidinone (NMP) as primary solvent, with anti-solvent of acetonitrile at 80° C., acetonitrile/water (2:1) at 60° C., or acetonitrile/water (1:1) at ambient temperature.

A representative XRPD pattern of Form C is provided in FIG. 14. In certain embodiments, Form C of Compound (I) is characterized by XRPD peaks, preferably significant peaks, located at, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all of the following approximate positions: 10.25, 13.01, 15.40, 17.13, 18.62, 20.56, 21.07, 21.96, 22.67, 24.84, 25.78, 26.17, 27.90, 29.50, 30.68, 31.04, 36.36, 37.89, and 39.05 degrees 2θ, plus or minus 0.10. In some embodiments, Form C has at least 8, at least 9, or at least 10 peaks. In some embodiments, Form C has at least 10 peaks.

In certain embodiments, Form C is characterized by peaks in an XRPD pattern located at 1, 2, 3, 4, 5, 6, 7, or all of the following approximate peak positions: 10.25±0.10, 13.01±0.10, 15.40±0.10, 20.56±0.10, 21.07±0.10, 24.84±0.10, 25.78±0.10, and 26.17±0.10 degrees 2θ. In certain embodiments, Form C is characterized by two or more peaks selected from 10.25±0.10, 13.01±0.10, 15.40±0.10, 20.56±0.10, 21.07±0.10, 24.84±0.10, 25.78±0.10, and 26.17±0.10 degrees 2θ. In certain embodiments, Form C is characterized by three or more peaks selected from 10.25±0.10, 13.01±0.10, 15.40±0.10, 20.56±0.10, 21.07±0.10, 24.84±0.10, 25.78±0.10, and 26.17±0.10 degrees 2θ. In certain embodiments, Form C is characterized by four or more peaks selected from 10.25±0.10, 13.01±0.10, 15.40±0.10, 20.56±0.10, 21.07±0.10, 24.84±0.10, 25.78±0.10, and 26.17±0.10 degrees 2θ. In certain embodiments, Form C is characterized by five or more peaks selected from 10.25±0.10, 13.01±0.10, 15.40±0.10, 20.56±0.10, 21.07±0.10, 24.84±0.10, 25.78±0.10, and 26.17±0.10 degrees 2θ. In certain embodiments, Form C is characterized by six or more peaks selected from 10.25±0.10, 13.01±0.10, 15.40±0.10, 20.56±0.10, 21.07±0.10, 24.84±0.10, 25.78±0.10, and 26.17±0.10 degrees 2θ. In certain embodiments, Form C is characterized by seven or more peaks selected from 10.25±0.10, 13.01±0.10, 15.40±0.10, 20.56±0.10, 21.07±0.10, 24.84±0.10, 25.78±0.10, and 26.17±0.10 degrees 2θ. In certain embodiments, Form C is characterized by all of the following peaks: 10.25±0.10, 13.01±0.10, 15.40±0.10, 20.56±0.10, 21.07±0.10, 24.84±0.10, 25.78±0.10, and 26.17±0.10 degrees 2θ. In certain embodiments, Form C is characterized by an XRPD pattern substantially similar to the XRPD pattern presented in FIG. 14.

In certain embodiments, provided herein is a solid form of Compound (I) having an XRPD pattern comprising peaks at approximately 10.25, 15.40, and 26.17 degrees 2θ. In further embodiments, the XRPD pattern further comprises peaks at approximately 20.56, 21.07, and 25.78 degrees 2θ. In even further embodiments, the XRPD pattern further comprises peaks at approximately 13.01 and 24.84 degrees 2θ.

In some embodiments, the XRPD peaks above (degrees 2θ peaks) are when analyzed using copper Kα radiation. In some embodiments, provided herein is a solid form of Compound (I), which has an XRPD pattern comprising peaks at approximately 10.25, 15.40, and 26.17 degrees 2θ when analyzed using copper Kα radiation.

Form C has an irregular block habit as shown in FIG. 15. Representative IR spectrum data of Form C is provided in FIG. 16. In certain embodiments, provided herein is a solid form of Compound (I), wherein the solid form is characterized by an IR spectrum substantially similar to the IR spectrum presented in FIG. 16.

Representative thermal characteristics of Form C are shown in FIG. 17. The TGA data shows weight loss of 0.12 wt % up to about 150° C. In certain embodiments, provided herein is a solid form of Compound (I), wherein the solid form is characterized by a TGA thermogram substantially similar to the TGA thermogram presented in FIG. 17. The DSC thermogram shows only one major event at slightly above 300° C. These data indicate that Form C is an anhydrate. In certain embodiments, the temperature maximum at slightly above 300° C. corresponds to decomposition of Compound (I). In certain embodiments, provided herein is a solid form of Compound (I), wherein the solid form is characterized by a DSC thermogram substantially similar to the DSC thermogram presented in FIG. 17.

Representative moisture sorption and desorption data of Form C are plotted in FIG. 18. In certain embodiments, form C exhibits a total mass change of 0.43% between 0% and 90% relative humidity, suggesting Form C is not hygroscopic. In certain embodiments, provided herein is a solid form of Compound (I), wherein the solid form is characterized by a DVS plot substantially similar to the DVS plot presented in FIG. 18. After undergoing the adsorption/desorption cycles, the XRPD pattern of Form C shows no change, as shown in FIG. 19. In certain embodiments, Form C is characterized by an XRPD pattern substantially similar to the XRPD pattern presented in FIG. 19.

Form conversion studies show that Form C typically converts to Form A at ambient temperature in a solvent system such as NMP/acetone/water (1:2.5:2.5). Form C also partially converts to Form A upon heating up to 220° C. for 4 hours, which is evidenced by the XRPD pattern of the resulting solid, as shown in FIG. 20. These observations suggest that Form C is monotropically related to Form A. In certain embodiments, Form A is characterized by an XRPD pattern substantially similar to the XRPD pattern presented in FIG. 20.

All of the combinations of the above embodiments are encompassed by this invention.

An XRPD stack plot of crystalline Forms A, B and C is provided in FIG. 21. In certain embodiments, Form A is characterized by an XRPD pattern substantially similar to the XRPD pattern presented in FIG. 21 Form A. In certain embodiments, Form B is characterized by an XRPD pattern substantially similar to the XRPD pattern presented in FIG. 21 Form B. In certain embodiments, Form C is characterized by an XRPD pattern substantially similar to the XRPD pattern presented in FIG. 21 Form C.

An IR overlay plot of crystalline Forms A, B and C is provided in FIG. 22. In certain embodiments, Form A is characterized by an IR spectrum substantially similar to the IR spectrum presented in FIG. 22 Form A. In certain embodiments, Form B is characterized by an IR spectrum substantially similar to the IR spectrum presented in FIG. 22 Form B. In certain embodiments, Form C is characterized by an IR spectrum substantially similar to the IR spectrum presented in FIG. 22 Form C.

5.2.4 Mixture of Forms

In some embodiments, provided herein are compositions comprising at least two crystalline forms of 3-(4-nitro-1-oxoisoindolin-2-yl)piperidine-2,6-dione. In some embodiments, the composition comprises two crystalline forms of 3-(4-nitro-1-oxoisoindolin-2-yl)piperidine-2,6-dione. In one embodiment, the composition comprises Form A and Form B. In another embodiment, the composition comprises Form A and Form C. In yet another embodiment, the composition comprises Form B and Form C.

The ratio of the two crystalline forms can be any ratio. In some embodiments, the ratio of the two crystalline forms is from about 5:1 to about 1:5. In some embodiments, the ratio of the two crystalline forms is from about 4:1 to about 1:4. In some embodiments, the ratio of the two crystalline forms is from about 3:1 to about 1:3. In some embodiments, the ratio of the two crystalline forms is from about 2:1 to about 1:2. In one embodiment, the ratio of the two crystalline forms is about 1:1. In another embodiment, the ratio of the two crystalline forms is about 2:1. In another embodiment, the ratio of the two crystalline forms is about 3:1. In another embodiment, the ratio of the two crystalline forms is about 4:1. In another embodiment, the ratio of the two crystalline forms is about 5:1.

In some embodiments, the composition comprises three crystalline forms of 3-(4-nitro-1-oxoisoindolin-2-yl)piperidine-2,6-dione. In one embodiment, the composition comprises Form A, Form B, and Form C. The ratio of the three crystalline forms can be any ratio. In one embodiment, the ratio of the three crystalline forms is about 1:1:1.

In one embodiment, the composition comprises more Form A than any other crystalline form or forms. In another embodiment, the composition comprises more Form B than any other crystalline form or forms. In yet another embodiment, the composition comprises more Form C than any other crystalline form or forms.

All of the combinations of the above embodiments are encompassed by this invention.

5.3 Methods of Use

Polymorphs provided herein exhibit physical characteristics that are beneficial for drug manufacture, storage or use. All polymorphs provided herein have utility as pharmaceutically active ingredients or intermediates thereof.

In some embodiments, provided herein are methods of treating and preventing a wide variety of diseases and conditions using polymorphs of 3-(4-nitro-1-oxoisoindolin-2-yl)piperidine-2,6-dione. In each of the methods, a therapeutically or prophylactically effective amount of the compound is administered to a patient in need of such treatment or prevention. Examples of such disease and conditions include, but are not limited to, diseases associated with undesired angiogenesis, cancer (e.g., solid and blood borne tumors), inflammatory diseases, autoimmune diseases, and immune diseases. Examples of cancers and pre-cancerous conditions include those described in U.S. Pat. Nos. 6,281,230 and 5,635,517 to Muller et al.; U.S. Pat. No. 7,189,740 (Treatment of Myelodisplastic Syndrome), U.S. Pat. No. 7,968,569 (Treatment of Various Types of Cancer), and U.S. Pat. No. 7,563,810 (Treatment of Myeloproliferative Diseases) to Zeldis. Examples of other diseases and disorders that can be treated or prevented using compositions provided herein are described in U.S. Pat. Nos. 6,235,756 and 6,114,335 to D'Amato; U.S. Application Publication Nos. 2005-0203142 A1 (Treatment of Pain Syndrome) and 2004-0091455 A1 (Treatment of Macular Degeneration) to Zeldis. The entirety of each of the patents and patent application publications cited herein is incorporated herein by reference.

Depending on the disease to be treated and the subject's condition, polymorphs provided herein can be administered by oral, parenteral (e.g., intramuscular, intraperitoneal, intravenous, ICV, intracisternal injection or infusion, subcutaneous injection, or implantation), inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. Because individual polymorphs have different dissolution, stability, and other properties, the optimal polymorph used in methods of treatment may depend on the route of administration. For example, forms that are readily soluble in aqueous solutions are preferably used to provide liquid dosage forms, whereas forms that exhibit great thermal stability may be preferred in the manufacture of solid dosage forms (e.g., tablets and capsules).

Although the physical characteristics of polymorphs can, in some cases, affect their bioavailability, amounts of the polymorphs that are therapeutically or prophylactically effective in the treatment of various disease and conditions can be readily determined by those of ordinary skill in the pharmacy or medical arts. In certain embodiments provided herein, a polymorph is administered orally and in a single or divided daily doses in an amount of from about 0.10 to about 150 mg/day, or from about 5 to about 25 mg/day. In other embodiments, a polymorph is administered every other day in an amount of from about 0.10 to about 150 mg/day, or from about 5 to about 25 mg/day.

In some embodiments, provided herein are methods of preparing 3-(4-amino-1-oxoisoindolin-2-yl)piperidine-2,6-dione, which comprise reduction of one or more polymorphs of 3-(4-nitro-1-oxoisoindolin-2-yl)piperidine-2,6-dione. Because individual polymorphs have different dissolution, stability, and other properties, the optimal polymorph used in methods of preparation of 3-(4-amino-1-oxoisoindolin-2-yl)piperidine-2,6-dione may depend on the reaction conditions. For example, the more stable form is often preferred for consistence of production and better physical properties.

5.4 Pharmaceutical Compositions and Dosage Form

In some embodiments, provided herein are pharmaceutical compositions and single unit dosage forms that can be used in methods of treatment and prevention, which comprise one or more polymorphs of 3-(4-nitro-1-oxoisoindolin-2-yl)piperidine-2,6-dione and optionally one or more excipients or diluents. Specific compositions and dosage forms are disclosed in the various patents and patent applications incorporated herein by reference. In one embodiment, a single dosage form comprises a polymorph (e.g., Form A) in an amount of about 5, 10, 25 or 50 mg.

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, or prodrug thereof. Pharmaceutical compositions and dosage forms provided herein can further comprise one or more excipients.

Pharmaceutical compositions and dosage forms provided herein can also comprise one or more additional active ingredients.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms provided herein will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms provided herein will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, in some embodiments, provided herein are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions provided herein can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

In some embodiments, provided herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, N.Y., NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

In some embodiments, provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms provided herein comprise a compound provided herein in an amount of from about 0.10 to about 500 mg. Typical dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

Typical dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the type of cancer being treated or managed, and the amount(s) of a compound provided herein and any optional additional active agents concurrently administered to the patient.

5.4.1 Oral Dosage Forms

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions provided herein is typically present in from about 50 to about 99 weight percent of the pharmaceutical composition or dosage form.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A solid oral dosage form provided herein comprises a compound provided herein, anhydrous lactose, microcrystalline cellulose, polyvinylpyrrolidone, stearic acid, colloidal anhydrous silica, and gelatin.

5.4.2 Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and U.S. Pat. No. 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein. In some embodiments, provided herein are single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.4.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms provided herein are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms provided herein. For example, cyclodextrin and its derivatives can be used to increase the solubility of an immunomodulatory compound provided herein and its derivatives. See, e.g., U.S. Pat. No. 5,134,127, which is incorporated herein by reference.

5.4.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms provided herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences,* 16th and 18th eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

6. EXAMPLES

6.1 Synthesis of Form A and/or Form B

A nitrogen-purged 1600 L Hastelloy reaction vessel was charged with methyl-2-bromomethyl-3-nitrobenzoate (61 kg, 1.0 mole eq.), racemic α-aminoglutarimide (36.6 kg, 1.0 mole eq.), and acetonitrile (478 kg). The mixture was stirred at ambient temperature and then cooled to 5-8° C. Sodium bicarbonate (46.7 kg, 2.5 mole eq.) was charged to the reaction vessel and the mixture was heated to reflux. The reaction vessel contents were vigorously stirred at reflux until the remaining brominated nitrobenzoate level is <3.0 mol % as determined by $^{1}$H-NMR. The reaction mixture was then cooled to 58-62° C.

A hydrochloric acid solution was prepared from concentrated hydrochloric acid (12.9 kg) and purified water (355 L) in a nitrogen-purged, stirred 1000 L Hastelloy vessel and heated to 58-62° C. A portion of this hydrochloric acid solution (329 L) was added to the reaction mixture in the 1600 L vessel over at least 10 minutes while maintaining the temperature at 58-62° C. The mixture was stirred for approximately 30 minutes, then pH of the reaction mixture was checked. If the pH was >6, 6.1 L aliquots of hydrochloric acid were added, while maintaining the temperature at approximately 58-62° C., until the pH of the reaction mixture was <6. The mixture was then cooled to ambient temperature over approximately 2.5 hours and stirred for an additional hour.

The solid was collected by vacuum/pressure filtration on an Oyster filter. The collected solid was washed on the Oyster filter with a mixture of acetone (76 kg) and purified water (90 kg), and de-liquored using vacuum pressure. The collected solid was washed with 147 kg of acetone and de-liquored using vacuum pressure. The solid was dried under vacuum in a VPD at <45° C. until loss on drying is <0.5% to provide 3-(4-nitro-1-oxoisoindolin-2-yl)piperidine-2,6-dione. The yield of a recent lot was 79.5%.

6.2 Equilibration

Equilibration studies using single, binary and ternary combinations of batch solvents (water, acetone, and acetonitrile) were investigated to mimic key steps in manufacturing 3-(4-nitro-1-oxoisoindolin-2-yl)piperidine-2,6-dione. Experimental details of solvent systems and temperature used in equilibration studies are listed in Table 1. Materials of 3-(4-nitro-1-oxoisoindolin-2-yl)piperidine-2,6-dione and solvent or solvent mixtures were added to a glass vial to achieve free-flowing slurry and allowed to equilibrate at the specified temperature. After equilibration for 8 days, the solid phase was separated via filtration. The solid phase was then dried under air and analyzed by XRPD.

TABLE 1

List of Experimental Conditions for Equilibration

| Solvent system | Temperature | Equilibration Time |
|---|---|---|
| Acetonitrile | 80° C. (or reflux) | 6 hours |
| Acetonitrile/water (2:1) | 60° C. | 6 hours |
| acetone | Ambient | 8 days |
| water | Ambient | 8 days |
| Acetone/water (1:1) | Ambient | 8 days |
| Acetonitrile/water (1:1) | Ambient | 8 days |
| Acetonitrile/water/acetone (1:1:1) | Ambient | 8 days |

A total of four batches of 3-(4-nitro-1-oxoisoindolin-2-yl)piperidine-2,6-dione were characterized by XRPD, DSC, TGA, ATR-FTIR and DVS, as described in section 6.5. The solid form represented by the batch 1 was designated as Form A; the solid form represented by the batch 4 was designated as Form B; the batches 2 and 3 were determined to be mixtures of Forms A and B, with Form B dominating the patterns. The equilibration experiments were performed using batches 2, 3 and 4, and the results are described in Table 2.

TABLE 2

Results for Equilibration Experiments

| Solvent system | Temperature | Time | Starting Batch # | Form by XRPD |
|---|---|---|---|---|
| Acetonitrile | 80° C. (or reflux) | 6 hours | 2 (A + B) | A |
| Acetonitrile/water (2:1) | 60° C. | 6 hours | 2 (A + B) | A |
| acetone | Ambient | 8 days | 2 (A + B) | A |
| water | Ambient | 8 days | 2 (A + B) | A |
| Acetone/water (1:1) | Ambient | 8 days | 2 (A + B) | A |
| Acetonitrile/water (1:1) | Ambient | 8 days | 2 (A + B) | A |
| Acetonitrile/water/acetone (1:1:1) | Ambient | 8 days | 2 (A + B) | A |
| Acetonitrile | 80° C. (or reflux) | 6 hours | 3 (A + B) | A |
| Acetonitrile/water (2:1) | 60° C. | 6 hours | 3 (A + B) | A |
| acetone | Ambient | 8 days | 3 (A + B) | A |
| water | Ambient | 8 days | 3 (A + B) | A |
| Acetone/water (1:1) | Ambient | 8 days | 3 (A + B) | A |
| Acetonitrile/water (1:1) | Ambient | 8 days | 3 (A + B) | A |
| Acetonitrile/water/acetone (1:1:1) | Ambient | 8 days | 3 (A + B) | A |
| Acetonitrile | 80° C. (or reflux) | 6 hours | 4 (B) | A |
| Acetonitrile/water (2:1) | 60° C. | 6 hours | 4 (B) | A |
| acetone | Ambient | 8 days | 4 (B) | A |
| water | Ambient | 8 days | 4 (B) | A |
| Acetone/water (1:1) | Ambient | 8 days | 4 (B) | A |
| Acetonitrile/water (1:1) | Ambient | 8 days | 4 (B) | A |
| Acetonitrile/water/acetone (1:1:1) | Ambient | 8 days | 4 (B) | A |

All solids isolated from these experiments afforded Form A, suggesting Form A is more thermodynamically stable form.

An XRPD stack plot of the four batches is provided in FIG. 23. In certain embodiments, Form A is characterized by an XRPD pattern substantially similar to the XRPD pattern presented in FIG. 23 batch 1. In certain embodiments, Form B is characterized by an XRPD pattern substantially similar to the XRPD pattern presented in FIG. 23 batch 4. In certain embodiments, a solid form of compound (I) is characterized by an XRPD pattern substantially similar to the XRPD pattern presented in FIG. 23 batch 2. In certain embodiments, a solid form of compound (I) is characterized by an XRPD pattern substantially similar to the XRPD pattern presented in FIG. 23 batch 3.

An IR overlay plot of the four batches is provided in FIG. 24. In certain embodiments, Form A is characterized by an IR spectrum substantially similar to the IR spectrum presented in FIG. 24 batch 1. In certain embodiments, Form B is characterized by an IR spectrum substantially similar to the IR spectrum presented in FIG. 24 batch 4. In certain embodiments, a solid form of compound (I) is characterized by an IR spectrum substantially similar to the IR spectrum presented in FIG. 24 batch 2. In certain embodiments, a solid form of compound (I) is characterized by an IR spectrum substantially similar to the IR spectrum presented in FIG. 24 batch 3.

6.3 Recrystallization

Recrystallization of 3-(4-nitro-1-oxoisoindolin-2-yl)piperidine-2,6-dione was performed using 1-methyl-2-pyrrolidinone (NMP) as primary solvent. Solid of 3-(4-nitro-1-oxoisoindolin-2-yl)piperidine-2,6-dione were dissolved in NMP with help of heat and filtered. The solvent systems listed in Table 1 were used as anti-solvent at the corresponding temperature. The results are summarized in Table 3.

TABLE 3

Recrystallization Results using NMP as Primary Solvent

| Anti-solvent | Temperature | Form by XRPD |
|---|---|---|
| Acetonitrile | 80° C. (or reflux) | C |
| Acetonitrile/water (2:1) | 60° C. | C |
| acetone | Ambient | B + C |
| water | Ambient | A + B + C |
| Acetone/water (1:1) | Ambient | B + C + peaks* |
| Acetone/water (1:1)** | Ambient | C |
| Acetonitrile/water (1:1) | Ambient | C |
| Acetonitrile/water (1:1)** | Ambient | C |
| Acetonitrile/water/acetone (1:1:1) | Ambient | B + C + peaks* |

*Additional diffraction peaks were observed at 7.1, 9.6, and 14.2° 2θ, which may represent a unique crystalline form.
**Experiments were repeated to confirm solid form observation and to generate additional materials.

Experiments from acetonitrile at 80° C., acetonitrile/water (2:1) at 60° C., or acetonitrile/water (1:1) at ambient temperature afforded unique XRPD pattern, which was designated as Form C. The other experiments afforded solids with mixture of forms. Solids from acetone/water (1:1) or acetonitrile/water/acetone (1:1:1) showed additional diffraction peaks at 7.1, 9.6, and 14.2° 2θ, which may represent another unique crystalline form. The anti-solvent recrystallization with acetonitrile/water (1:1) or acetone/water (1:1) at ambient were repeated to confirm the solid form observation and to generate additional materials for further characterization. The solid form the repeated experiment using acetonitrile/water (1:1) as antisolvent was confirmed to be Form C. The attempt to regenerate the additional diffraction peaks using acetone/water (1:1) as antisolvent didn't generate a unique pattern, but afforded solid of Form C.

6.4 Additional Form Conversion Experiments

Additional form conversion studies were performed and the results are summarized in Table 4.

TABLE 4

Results from Additional Form Conversion Experiments

| Starting Form | Condition | XRPD Result |
|---|---|---|
| Form B | Heated to 220° C. for 4 hours | Form A |
| Form C | Heated to 220° C. for 4 hours | Form A + C |
| Form C | Slurry in NMP/Acetone/water at ambient for 5 days | Form A + C |
| Form C | Slurry in NMP/Acetone/water at ambient for 10 days | Form A + C |

6.5 Characterization 6.5.1 X-Ray Powder Diffraction (XRPD)

All of the solid samples generated in the polymorph screen were analyzed by XRPD. XRPD analysis was conducted on a PANalytical Empyrean or a Thermo ARL X'TRA X-ray powder diffractometer using Cu Kα radiation at 1.54 Å.

The PANalytical Empyrean instrument was equipped with a fine focus X-ray tube. The voltage and amperage of the X-ray generator were set at 45 kV and 40 mA, respectively. The divergence slits were set at 1/16° and 1/8 °, and the receiving slits was set at 1/16°. Diffracted radiation was measured using a Pixel 2D detector. A theta-two theta continuous scan was set at step size 0.013 from 3° to 40° 2θ with sample spinning rate at 4. A sintered alumina standard was used to check the peak positions.

The Thermo ARL X'TRA instrument was equipped with a fine focus X-ray tube. The voltage and amperage of the X-ray generator were set at 45 kV and 40 mA, respectively. The divergence slits were set at 4 mm and 2 mm and the measuring slits were set at 0.5 mm and 0.2 mm. Diffracted radiation was measured using a Peltier-cooled Si (Li) solid-state detector. A theta-two theta continuous scan at 2.40°/min (0.5 sec/0.02° step) from 1.5° to 40° 2θ was used. A sintered alumina standard was used to check the peak positions.

The peaks for Form A, Form B, and Form C XRPD patterns were identified. XRPD patterns are provided in FIG. 1 (Form A), FIG. 7 (Form B), and FIG. 14 (Form C). Peak values and intensity values are provided in the table below. For samples with only one XRPD pattern and no other means to evaluate whether the sample provides a good approximation of the powder average, peak tables contain data identified only as "Prominent Peaks". These peaks are a subset of the entire observed peak list. Prominent peaks are selected from observed peaks by identifying preferably non-overlapping, low-angle peaks, with strong intensity. Although peaks are labeled on diffraction patterns and/or listed in tables, for technical reasons, different rounding algorithms were used to round each peak to the nearest 0.1° or 0.01° 2θ, depending upon the instrument used to collect the data and/or the inherent peak resolution. The location of the peaks along the x-axis (° 2θ) were rounded to one or two significant figures after the decimal point based upon the above criteria. Peak position variabilities are given to within ±0.1° 2θ based upon recommendations outlined in the USP discussion of variability in x-ray powder diffraction.

TABLE 5

XRPD Peak Table of Form A

| No. | Pos. [°2Th.] | d-spacing [Å] | Height [cts] | Rel. Int. [%] |
|---|---|---|---|---|
| 1 | 10.30 | 8.59 | 14766.88 | 100.00 |
| 2 | 10.59 | 8.35 | 1959.09 | 13.27 |
| 3 | 12.80 | 6.91 | 867.96 | 5.88 |
| 4 | 13.03 | 6.80 | 2195.07 | 14.86 |
| 5 | 14.85 | 5.96 | 2980.16 | 20.18 |
| 6 | 15.15 | 5.85 | 4172.06 | 28.25 |
| 7 | 16.40 | 5.41 | 1529.30 | 10.36 |
| 8 | 16.93 | 5.24 | 2097.79 | 14.21 |
| 9 | 18.39 | 4.82 | 3837.08 | 25.98 |
| 10 | 18.55 | 4.78 | 3001.13 | 20.32 |
| 11 | 20.71 | 4.29 | 2092.99 | 14.17 |
| 12 | 21.08 | 4.22 | 844.00 | 5.72 |
| 13 | 21.28 | 4.18 | 3167.38 | 21.45 |
| 14 | 21.53 | 4.13 | 286.77 | 1.94 |
| 15 | 22.08 | 4.03 | 2934.77 | 19.87 |
| 16 | 22.63 | 3.93 | 959.05 | 6.49 |
| 17 | 24.91 | 3.57 | 6432.72 | 43.56 |
| 18 | 25.40 | 3.51 | 2281.35 | 15.45 |
| 19 | 25.78 | 3.46 | 2798.30 | 18.95 |
| 20 | 26.25 | 3.39 | 11225.20 | 76.02 |
| 21 | 27.22 | 3.28 | 82.18 | 0.56 |
| 22 | 28.70 | 3.11 | 494.31 | 3.35 |
| 23 | 29.55 | 3.02 | 3625.21 | 24.55 |
| 24 | 30.02 | 2.98 | 350.35 | 2.37 |
| 25 | 30.31 | 2.95 | 378.60 | 2.56 |
| 26 | 30.69 | 2.91 | 567.71 | 3.84 |
| 27 | 31.00 | 2.88 | 1093.68 | 7.41 |
| 28 | 31.56 | 2.84 | 350.95 | 2.38 |
| 29 | 32.43 | 2.76 | 549.38 | 3.72 |
| 30 | 33.17 | 2.70 | 148.43 | 1.01 |
| 31 | 34.34 | 2.61 | 527.70 | 3.57 |

TABLE 5-continued

XRPD Peak Table of Form A

| No. | Pos. [°2Th.] | d-spacing [Å] | Height [cts] | Rel. Int. [%] |
|---|---|---|---|---|
| 32 | 34.96 | 2.57 | 93.08 | 0.63 |
| 33 | 35.78 | 2.51 | 405.55 | 2.75 |
| 34 | 36.68 | 2.45 | 350.54 | 2.37 |
| 35 | 37.95 | 2.37 | 131.97 | 0.89 |
| 36 | 38.30 | 2.35 | 115.07 | 0.78 |
| 37 | 39.12 | 2.30 | 621.07 | 4.21 |

TABLE 6

XRPD Peak Table of Form B

| No. | Pos. [°2Th.] | d-spacing [Å] | Height [cts] | Rel. Int. [%] |
|---|---|---|---|---|
| 1 | 10.32 | 8.57 | 4126.10 | 10.64 |
| 2 | 12.54 | 7.06 | 87.15 | 0.22 |
| 3 | 13.94 | 6.35 | 38772.77 | 100.00 |
| 4 | 14.63 | 6.06 | 7910.54 | 20.40 |
| 5 | 15.46 | 5.73 | 2432.00 | 6.27 |
| 6 | 15.72 | 5.64 | 4052.98 | 10.45 |
| 7 | 16.83 | 5.27 | 1589.96 | 4.10 |
| 8 | 17.14 | 5.17 | 14501.45 | 37.40 |
| 9 | 18.82 | 4.72 | 3347.54 | 8.63 |
| 10 | 19.07 | 4.65 | 257.01 | 0.66 |
| 11 | 20.68 | 4.29 | 2889.94 | 7.45 |
| 12 | 20.99 | 4.23 | 383.02 | 0.99 |
| 13 | 21.35 | 4.16 | 232.00 | 0.60 |
| 14 | 21.72 | 4.09 | 324.95 | 0.84 |
| 15 | 22.14 | 4.02 | 326.51 | 0.84 |
| 16 | 22.48 | 3.96 | 1210.79 | 3.12 |
| 17 | 22.69 | 3.92 | 2963.80 | 7.64 |
| 18 | 23.36 | 3.81 | 238.82 | 0.62 |
| 19 | 24.27 | 3.67 | 460.76 | 1.19 |
| 20 | 24.79 | 3.59 | 1654.72 | 4.27 |
| 21 | 25.46 | 3.50 | 274.53 | 0.71 |
| 22 | 25.86 | 3.45 | 710.64 | 1.83 |
| 23 | 26.26 | 3.39 | 2200.96 | 5.68 |
| 24 | 26.99 | 3.30 | 668.91 | 1.73 |
| 25 | 27.33 | 3.26 | 461.88 | 1.19 |
| 26 | 27.69 | 3.22 | 2960.01 | 7.63 |
| 27 | 28.01 | 3.19 | 1912.16 | 4.93 |
| 28 | 28.70 | 3.11 | 308.94 | 0.80 |
| 29 | 29.45 | 3.03 | 603.29 | 1.56 |
| 30 | 30.49 | 2.93 | 2202.15 | 5.68 |
| 31 | 30.56 | 2.93 | 1746.82 | 4.51 |
| 32 | 31.21 | 2.86 | 261.71 | 0.67 |
| 33 | 32.12 | 2.78 | 359.23 | 0.93 |
| 34 | 33.13 | 2.70 | 127.53 | 0.33 |
| 35 | 33.66 | 2.66 | 123.91 | 0.32 |
| 36 | 34.64 | 2.59 | 413.08 | 1.07 |
| 37 | 35.35 | 2.54 | 106.99 | 0.28 |
| 38 | 35.73 | 2.51 | 251.84 | 0.65 |
| 39 | 36.33 | 2.47 | 569.91 | 1.47 |
| 40 | 36.97 | 2.43 | 589.65 | 1.52 |
| 41 | 37.98 | 2.37 | 331.89 | 0.86 |
| 42 | 39.15 | 2.30 | 555.03 | 1.43 |

TABLE 7

XRPD Peak Table of Form C

| No. | Pos. [°2Th.] | d-spacing [Å] | Height [cts] | Rel. Int. [%] |
|---|---|---|---|---|
| 1 | 10.25 | 8.63 | 3535.01 | 100.00 |
| 2 | 13.01 | 6.81 | 231.55 | 6.55 |
| 3 | 15.40 | 5.76 | 1939.24 | 54.86 |
| 4 | 17.13 | 5.18 | 82.49 | 2.33 |
| 5 | 18.62 | 4.77 | 78.79 | 2.23 |
| 6 | 20.56 | 4.32 | 597.87 | 16.91 |
| 7 | 21.07 | 4.22 | 401.69 | 11.36 |
| 8 | 21.96 | 4.05 | 101.65 | 2.88 |
| 9 | 22.67 | 3.92 | 109.31 | 3.09 |

TABLE 7-continued

XRPD Peak Table of Form C

| No. | Pos. [°2Th.] | d-spacing [Å] | Height [cts] | Rel. Int. [%] |
|---|---|---|---|---|
| 10 | 23.38 | 3.81 | 32.12 | 0.91 |
| 11 | 24.84 | 3.58 | 271.03 | 7.67 |
| 12 | 25.78 | 3.46 | 655.67 | 18.55 |
| 13 | 26.17 | 3.41 | 1836.63 | 51.96 |
| 14 | 27.90 | 3.20 | 54.64 | 1.55 |
| 15 | 29.50 | 3.03 | 147.04 | 4.16 |
| 16 | 30.68 | 2.91 | 165.02 | 4.67 |
| 17 | 31.04 | 2.88 | 90.21 | 2.55 |
| 18 | 35.56 | 2.52 | 33.01 | 0.93 |
| 19 | 36.36 | 2.47 | 45.85 | 1.30 |
| 20 | 37.89 | 2.37 | 49.90 | 1.41 |
| 21 | 39.05 | 2.31 | 137.81 | 3.90 |

6.5.2 Differential Scanning Calorimetry (DSC)

DSC analyses were performed on a TA instrument Q2000 Differential Scanning calorimeter. Indium was used as the calibration standard. Approximately 2-5 mg of sample was placed into a DSC pan. The sample was heated under nitrogen at a rate of 10° C./min, up to a final temperature of 350° C. Melting points were reported as the extrapolated onset temperatures.

6.5.3 Thermogravimetric Analysis (TGA)

TGA analyses were performed on a TA instrument Q5000 Thermogravimetric Analyzer. Calcium oxalate was used for a performance check. Approximately 2-10 mg of accurately weighed sample was placed on a pan and loaded into the TGA furnace. The sample was heated under nitrogen at a rate of 10° C./min, up to a final temperature of 300° C.

6.5.4 Attenuated Total Reflection Fourier-Transform Infrared Analysis (ATR-FTIR)

FTIR analyses were performed on the samples "as is" using an attenuated total reflection (ATR) attachment on a Nicolet 6700 FTIR spectrometer. After a background of ambient lab conditions was obtained, samples were placed on the ATR, compressed with the anvil, and spectrum acquired.

6.5.5 Miniature Scanning Electron Microscope (Mini SEM)

Morphology analysis of the samples was carried out on an Even Mini SEM. Small amounts of samples were dispersed on a sample holder, and then coating with gold viewed with 200× and 1000× magnification.

6.5.6 Dynamic Vapor Sorption (DVS)

Hygroscopicity was determined on a Surface Measurement Systems DVS. Typically a sample size of 5-30 mg was loaded into the DVS instrument sample pan and the sample was analyzed on a DVS automated sorption analyzer at 25° C. The relative humidity was increased from 0% to 90% RH at 10% RH step. The relative humidity was then decreased in a similar manner to accomplish a full adsorption/desorption cycle.

The entire scope of this invention is not limited by the specific examples described herein, but is more readily understood with reference to the appended claims.

What is claimed is:

1. A solid form of crystalline Form C of the compound of Formula (I):

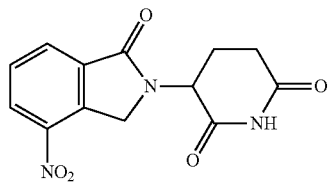
(I)

having an X-ray powder diffraction pattern having peaks located at 3, 4, 5, 6, 7, or all of the following approximate peak positions: 10.25±0.10, 13.01±0.10, 15.40±0.10, 20.56±0.10, 21.07±0.10, 24.84±0.10, 25.78±0.10, and 26.17±0.10 degrees 2θ, or a pharmaceutically acceptable salt, hydrate, or solvate thereof.

2. The solid form of claim 1 having an X-ray powder diffraction pattern comprising peaks at approximately 10.25, 15.40, and 26.17 degrees 2θ.

3. The solid form of claim 2 having an X-ray powder diffraction pattern further comprising peaks at approximately 20.56, 21.07, and 25.78 degrees 2θ.

4. The solid form of claim 3 having an X-ray powder diffraction pattern further comprising peaks at approximately 13.01 and 24.84 degrees 2θ.

5. The solid form of claim 1 having an X-ray powder diffraction pattern that is substantially similar to the XRPD pattern presented in FIG. 14.

* * * * *